US011541237B2

(12) United States Patent
Levin

(10) Patent No.: US 11,541,237 B2
(45) Date of Patent: Jan. 3, 2023

(54) METHODS FOR IMPROVING SHOULDER RANGE OF MOTION AND FUNCTIONALITY

(71) Applicant: BHL PATENT HOLDINGS LLC, Towanda, PA (US)

(72) Inventor: Bruce H Levin, Philadelphia, PA (US)

(73) Assignee: BHL PATENT HOLDINGS LLC, Towanda, PA (US)

( * ) Notice: Subject to any disclaimer, the term of this patent is extended or adjusted under 35 U.S.C. 154(b) by 316 days.

(21) Appl. No.: 15/998,669

(22) Filed: Aug. 15, 2018

(65) Prior Publication Data

US 2018/0361154 A1 Dec. 20, 2018

Related U.S. Application Data

(63) Continuation-in-part of application No. 14/777,145, filed as application No. PCT/US2014/031025 on Mar. 18, 2014, now abandoned.
(Continued)

(51) Int. Cl.
*A61N 1/36* (2006.01)
*A61N 1/04* (2006.01)
(Continued)

(52) U.S. Cl.
CPC ........ *A61N 1/36071* (2013.01); *A61K 31/167* (2013.01); *A61K 31/445* (2013.01);
(Continued)

(58) Field of Classification Search
CPC ........... A61N 1/36071; A61N 1/36021; A61N 1/0484; A61N 1/3787; A61M 19/00
(Continued)

(56) References Cited

U.S. PATENT DOCUMENTS

| 2,123,980 A | 7/1938 | Warwick |
| 2,182,071 A | 12/1939 | Crossley |

(Continued)

FOREIGN PATENT DOCUMENTS

| EP | 0069427 A2 | 7/1982 |
| EP | 0970813 A2 | 6/1999 |

(Continued)

OTHER PUBLICATIONS www.cefaly.com (Frequently Asked Questions, Accessed Oct. 15, 2017) (Year: 2017).

*Primary Examiner* — Amanda K Hulbert
*Assistant Examiner* — Philip C Edwards
(74) *Attorney, Agent, or Firm* — Debora Plehn-Dujowich; Eckert Seamans Cherin & Mellott, LLC

(57) ABSTRACT

Methods, apparatus, compositions and kits for inhibiting a disorder in a human patient, including non-cerebral neurovascular disorder or muscular headache pain, or loss of motor or sensory function, sympathetic tone or range or fluidity of motion that affect a nerve pathway at more than one locus associated with the disorder to inhibit the disorder. Alternatively or in addition, neuropathy associated with a disorder is treatable by palpating to determine a Keystone nerve essential to the neuropathy, applying pressure to determine a point of maximum discomfort or trigger of increased symptoms to identify a Levin Sign as a locus of initial intervention, and intervening to treat the neuropathy at the location of the Levin Sign by administering a pharmaceutically active agent, internal implanted or external neuro stimulation affecting the nerve pathway to inhibit the neuropathy.

1 Claim, 7 Drawing Sheets

Related U.S. Application Data

(60) Provisional application No. 61/813,432, filed on Apr. 18, 2013, provisional application No. 61/793,123, filed on Mar. 15, 2013, provisional application No. 62/545,536, filed on Aug. 15, 2017.

(51) Int. Cl.
| | | |
|---|---|---|
| *A61N 1/378* | (2006.01) | |
| *A61K 31/445* | (2006.01) | |
| *A61P 29/00* | (2006.01) | |
| *A61P 25/06* | (2006.01) | |
| *A61P 25/02* | (2006.01) | |
| *A61K 31/167* | (2006.01) | |
| *A61M 19/00* | (2006.01) | |
| *A61M 11/00* | (2006.01) | |
| *A61M 15/08* | (2006.01) | |

(52) U.S. Cl.
CPC ........... *A61M 19/00* (2013.01); *A61N 1/0484* (2013.01); *A61N 1/36021* (2013.01); *A61N 1/3787* (2013.01); *A61P 25/02* (2018.01); *A61P 25/06* (2018.01); *A61P 29/00* (2018.01); *A61M 11/007* (2014.02); *A61M 15/08* (2013.01); *A61M 2202/048* (2013.01); *A61M 2210/0618* (2013.01); *A61N 1/36139* (2013.01)

(58) Field of Classification Search
USPC .......................................................... 607/46
See application file for complete search history.

(56) References Cited

U.S. PATENT DOCUMENTS

| | | |
|---|---|---|
| 5,898,035 A | 4/1999 | Inchiosa et al. |
| 6,526,318 B1 | 2/2003 | Ansarinia |
| 7,813,804 B1* | 10/2010 | Jaax .................... A61N 1/36071 |
| | | 607/46 |
| 8,137,711 B2 | 3/2012 | Wolicki |
| 8,702,584 B2 | 4/2014 | Rigaux et al. |
| 8,712,534 B2 | 4/2014 | Wei |
| 2003/0014088 A1* | 1/2003 | Fang .................. A61N 1/36017 |
| | | 607/48 |
| 2004/0158294 A1 | 8/2004 | Thompson |
| 2006/0047326 A1* | 3/2006 | Wheeler ............ A61N 1/36014 |
| | | 607/48 |
| 2009/0210028 A1 | 8/2009 | Rigaux et al. |
| 2013/0226275 A1* | 8/2013 | Duncan ................ A61N 1/0492 |
| | | 607/152 |

FOREIGN PATENT DOCUMENTS

| | | |
|---|---|---|
| WO | 2005056112 A1 | 6/2005 |
| WO | 2005117981 A1 | 12/2005 |

* cited by examiner

METHODS FOR IMPROVING SHOULDER RANGE OF MOTION AND FUNCTIONALITY

CROSS-REFERENCE TO RELATED APPLICATIONS

This application is a continuation-in-part of U.S. patent application Ser. No. 14/777,145, filed Sep. 15, 2015, which is the U.S. national stage application of PCT/US2014/031025 filed Mar. 18, 2014, which claims priority from Provisional Application No. 61/793,123, filed Mar. 15, 2013 and Provisional Application No. 61/813,432 filed Apr. 18, 2013; and claims benefit of U.S. Patent Application No. 62/545,536, filed Aug. 15, 2017, the disclosures of which are hereby incorporated herein by reference in their entireties.

BACKGROUND OF THE INVENTION

This invention relates to compositions, devices, kits and methods for treating neuropathies and related disorders, including those involving a "Keystone nerve" (as defined hereinafter), including inhibiting pain associated with them, or for improving functionality, such as functionality resulting from the loss of motor or sensory function, sympathetic tone or range or fluidity of motion, following or as a result of trauma, neoplasm, cancer, surgery, small fiber peripheral neuropathy or nerve damage or compromise, or sympathetic dysfunction involving anything other than a cerebral neurovascular disorder (as defined hereinafter) or a muscular headache, such as but not limited to at least one of a disorder comprising pain or loss of motor or sensory function, sympathetic tone or range or fluidity of motion or trigeminal neuralgia (hereinafter generally a "disorder") of the face, head, neck, oropharynx, oral, dental, temporomandibular joint or musculature (TMJ), thorax, abdomen, pelvis, genitalia, shoulder, back, elbow, wrist, hip, knee, ankle or other joints, limbs or musculature or connective tissue.

Any single one or any combination of these disorders, neuropathies, dysfunctions, indications, conditions or symptoms are treated according to this invention by affecting, such as by anesthetizing, blocking or disrupting a nerve pathway associated with the neuropathy, pain, disorder or dysfunction, such as but not limited to a dorsonasal nerve structure, a nerve of the head and neck, a nerve of the lower extremities, any portion of the spinal cord, suprascapular nerve, radial nerve, median nerve, ulnar nerve, musculocutaneous nerve, or peripheral or sympathetic nerves, including branches and small fibers of such nerves, associated with the neuropathy, pain, disorder or dysfunction in any manner to inhibit the neuropathy, pain, disorder or dysfunction. The nerve pathway may be anesthetized, blocked or disrupted by any of the following interventions: (a) performing acupuncture upon the nerve structure; (b) surgically intervening to disrupt or sever nerve structures; (c) by applying an electrical potential or current, including low level current, or electromagnetic radiation to the nerve pathway externally or internally, such as transepithelial (also known as transcutaneous) electrical neural stimulation or implantable and preferably a miniaturized electronic stimulation device or energy generating device stimulator such as microelectromechanical systems (MEMS), nanoelectromechanical systems (NEMS), magnetic induction, radio frequency radiation or visible or non-visible light frequency, x-rays, proton bombardment, ultrasound, infrasound, near infrared or laser, applying heat, applying cold, or mechanical massage; or any other technique for stimulating an organ, tissue or nerve pathway to inhibit the disorder, neuropathy, indication, condition or symptom. (any one or more interventions of category (c) will be referred to hereinafter as a "Stimulation Technique" and any one or more devices used to stimulate, sense a condition of or monitor a function of an organ, tissue or nerve pathway or for any purpose set forth herein will referred to as a "Stimulation Device"); or (d) administering by any suitable means, such as parenterally, topically, transcutaneously, intranasally or dorsonasally, a local anesthetic or other pharmaceutically active agent capable of anesthetizing, blocking or disrupting any of the foregoing disorders, alone or together, to the areas containing or affecting the nerve pathway. Any one or any combination of two or more of these types of interventions (a) to (d) will be referred to herein broadly as an "Intervention" or "Interventions" to avoid having to repeat them throughout this application.

Peripheral nerve injections, stimulation, neuroaugmentation or neuromodulation involve a distinct nerve or ganglion structure which is targeted by the Interventions. One aspect of this invention targets peripheral nerve fibers or other structures physiologically or anatomically related to a given nerve structure or pathway, with or without having to directly target the specific distinct nerve structure itself. Thus, it is easier, safer and more practical to do and is surprisingly effective.

Another aspect of this invention is based on a procedure that involves reviewing the patient's putative mechanism of injury, and to try to grade the different quality and intensity of patient symptoms, and guide the physical examination accordingly. The diagnosis takes into account putative or known mechanisms of injury, patient initial and subsequent complaints in terms of quality and location, duration, timing, and factors affecting severity and quality of pain or other symptoms. The examination seeks and/or evaluates the presence of swelling, temperature changes, allodynia, range of motion, limbricity and sensory and motor function.

In particular, steady increase of pressure to palpation is applied along the course of certain major nerves in the area of the trauma or other neuropathy, such as the sural, saphenous, common popliteal, antebrachial cutaneous, radial nerves, among others for example, in order to identify what the inventor has coined as the Keystone nerve or compartment or body segment which is triggering and essential to the wider propagation or distribution of pathology and symptoms, which includes pathology affecting of other nerves, structures and or locations (hereinafter the "Keystone nerve"). The Keystone nerve may or may not have been the nerve or compartment initially injured or damaged or degenerated, but plays a significant role in the continuing pathology.

As indicated above, the Keystone nerve is identified by mild to moderate pressure applied to the course of putative Keystone nerves or structures to identify the Keystone nerve. The point of at least one of maximum discomfort or trigger of increased trophic symptoms or findings is the locus of initial intervention. This point is coined by the inventor as the "Levin Sign," distinct from mere tender points or trigger points and distinct from the Tinnel's sign, because direct application of increasing pressure is applied to determine the Keystone nerve and the Levin Sign, as opposed to striking a nerve superficially in a percussive manner as done for the Tinnel's sign.

Once the Keystone nerve and Levin Sign are identified, intervention may include any or all of the foregoing Interventions.

U.S. Pat. No. 6,432,986 relates to treating a cerebral neurovascular disorder (CNvD) by dorsonasally administering to the patient over a period of time of less than about one half hour a long-acting local anesthetic in an amount effective to anesthetize a dorsonasal nerve structure to inhibit the CNvD for greater than one hour. CNvDs are characterized by one or more disturbances in the normal functioning of at least one component of the cerebral vascular or nervous system in a human. Headache is a common symptom of numerous diseases and disorders including, but not limited to, migraine, muscle tension, systemic or intracranial infection, intracranial tumor, head injuries, severe hypertension, cerebral hypoxia, certain diseases of the eyes, nose, throat, teeth, and ears, and head pain for which no cause can be determined. This patent focused, among other things, on treating tinnitus, cerebrovascular spasm, seizure, a disorder manifested during or after and associated with an acute ischemic event, and a neurovascular headache such migraine, cluster headaches, and headaches associated with a vascular disease, as well as muscular headaches.

U.S. Pat. No. 6,491,940 relates to various embodiments of dorsonasal drug delivery devices having a shape which conforms to the shape of the nasal cavity of a human, which, in some embodiments have an anatomically adapted dorsonasal delivery nozzle, and methods for dorsonasally administering compositions using the devices.

U.S. Pat. No. 7,799,337 relates to methods of intranasally administering a composition directly to a selected intranasal location of a human patient other than for effecting a block of the sphenopalatine ganglion, by using an intranasal delivery device by which the composition selectively enters at least one of (i) the inferior boundary of the nasopharynx, (ii) sinuses via pathways specific thereto, and (iii) cerebral tissue selected from the group consisting of cerebral spinal fluid, a cerebral neuronal structure and cerebral vasculature, via pathways specific thereto.

U.S. Pat. No. 8,224,438 relates to a method of inhibiting a CNvD, such as migraine or headache associated with pain in a human patient by implanting an electronic neural stimulator in patient tissue adjacent a dorsonasal nerve structure and energizing the implanted electronic neural stimulator, so as to inhibit pain.

CNvDs are characterized by one or more disturbances in the normal functioning of at least one component of the cerebral vascular or nervous system in a human. CNvDs include, for example, migraine, cluster headaches, other headaches of neurovascular etiology, tinnitus, and cerebrovascular spasm. Human patients afflicted with a CNvD experience a single episode of the disorder, recurrent episodes, persistent episodes, or some combination of these patterns. An individual episode is designated an acute CNvD.

Peripheral Neuropathy

Neuropathies may result from metabolic, toxic, traumatic, postsurgical, oncologic, or degenerative spinal or other insults. Neuropathies compromise sensory, motor, autonomic and other functions and often result in severely compromised function and pain and dyssesthesias. They are very difficult to treat and patients often require ongoing high dose opioid and other medications and have poor responses to these and other therapies. Either spinal cord stimulation or peripheral nerve stimulation is used. The methods described herein allow for a novel approach to interrupting abnormal nerve conduction by utilizing a field sympathetic block around a given nerve or nerves which is safer and easier to perform than current methods and for neurostimulation techniques that are unique and/or easier to accomplish. Interestingly, the identification of a key neural component of a pathological process will normalize eurological function of a different nerve and decrease pain and dysesthesias in the distribution of that different nerve.

Phantom limb pain is pain that is felt in a body portion that is not present. It results from alterations of central pain processing and may be treated by the methods disclosed herein.

Complex Regional Pain Syndrome

Complex regional pain syndrome ("CRPS") is a nerve disorder characterized by at least one, and often a combination of symptoms of intense burning pain, stiffness, swelling, pathological changes in bone and skin, excessive sweating, tissue swelling, extreme sensitivity to touch and discoloration, changes in skin texture, motor disability, with decreased ability to move affected body part, and changes in nail and hair growth patterns. CRPS most often affects the hand, arms, legs and feet. There are two types of CRPS. Type I CRPS, also known as reflex sympathetic disorder ("RSD"), is triggered by tissue injury where there is no identifiable underlying nerve injury, while Type II CRPS refers to cases where a specific nerve is damaged, for example where a high-velocity impact (such as a bullet wound) occurred at the site and is clearly associated with nerve injury. Type II used to be called "causalgia." CRPS usually develops in an injured limb, such as a broken leg. However, many cases involve only a minor, seemingly inconsequential injury, such as a sprain. In some cases, no precipitating event can be identified. There is no known cure, but there are various types of palliative treatments, including, among others, topical analgesics, antidepressants, corticosteroids and opioids to relieve pain. However, no single drug or combination of drugs has produced consistent long-lasting improvement in symptoms. Other treatments may include physical therapy, sympathetic nerve block, spinal cord stimulation, neuroaugmentation and intrathecal drug pumps to deliver opioids and local anesthetic agents via the spinal cord. These have not been optimally effective for many patients.

Anatomy of the Nasal Cavity

The structures associated with the nasal cavity are described, for example, in Williams et al. (eds., 1980, Gray's Anatomy, 36th ed., W.B. Saunders Co., Philadelphia, 1062-1065), especially at FIGS. 3.78, 3.79, 3.80, 7.239, and 7.240 and the accompanying text. FIG. 1 herein is a diagram depicting the approximate location of the SPG in relation to the nasal cavity of a human.

The sphenopalatine ganglion (hereinafter, the "SPG") is, in some texts, designated the "pterygopalatine ganglion." The position, origin, branches, and distribution of the SPG may be understood by examining FIGS. 7.177, 7.178, 7.179, and 7.181 and the accompanying text in Williams et al. (supra).

As the cited figures and text describe, the SPG is located below a region of epithelium in the posterior portion of the nasal cavity, inferior to and including the sphenoethmoidal recess, and is therefore not readily accessible via the nostril.

Ropivacaine is a recently introduced amino amide local anesthetic that is commercially available as the S (levo) enantiomer (Lee et al., 1989, Anesth. Analg. 69:736-738). Ropivacaine allows differential nerve block and exhibits intermediate distribution and clearance and a better systemic toxicity profile compared with other similar relatively long acting potent local anesthetics. In addition, ropivacaine also exhibits inherent vasoactive properties (deJong, 1995, Reg. Anesth. 20:4 7 4-481; Santos et al., 1990, Anesth. Analg. 70:262-266). Ropivacaine-HCl is commercially available as 0.25%, 0.5%, 0.75% and 1.0% (w/v) solution (NAROPIN™, Astra USA, Inc., Westborough, Mass.), and has been described, for example in international patent application publication number WO 85/00599.

Local anesthetics are known to block the generation and the conduction of nerve impulses, presumably by increasing the threshold for electrical excitation in the nerve, by slowing the propagation of nerve impulses, and by reducing the rate of rise of the action potential of the nerve. In general, the progression of anesthesia is related to the diameter, degree of myelination, and conduction frequency and velocity of affected nerve fibers. Generally, the order of loss of nerve function is as follows: (1) sympathetic and parasympathetic function, temperature and pain, and (2) touch, and, where applicable, (3) proprioception, and (4) skeletal muscle tone.

The rate of systemic absorption in a patient of a local anesthetic is dependent upon the total dose, the concentration, and the identity of the local anesthetic administered to the patient, the route of administration, the vascularity of the site of administration, and the presence or absence of vasoconstrictors such as epinephrine in the anesthetic composition. A dilute concentration of epinephrine (e.g., 1:200,000 or 5 micrograms per milliliter) usually reduces the rate of absorption and peak plasma concentration of the local anesthetic, sometimes prolonging the duration of the anesthetic effect.

The duration of the anesthetic effect at a given site of administration of a local anesthetic is dependent upon the total dose, the concentration, and the identity of the local anesthetic administered to the patient, the rate of systemic absorption, and often the presence or absence of a vasoconstricting or other agent in the anesthetic composition.

Systemic administration of a local anesthetic is not a practical method for delivery of the local anesthetic to provide lasting relief of pain or other symptoms and indications associated with traumatic neuropathies and related disorders in a human patient, due to known adverse reactions, occasionally including acute emergencies, associated therewith.

There remains a significant unmet need for effective methods of treating pain other than pain associated with CNvDs. One aspect of the present invention provides compositions and methods which satisfy this need.

There also remains a significant urgent need for effective compositions and methods of treating pain not associated with muscular headaches. The present invention provides compositions, devices and methods which satisfy this need.

BRIEF SUMMARY OF THE INVENTION

Figure 1:
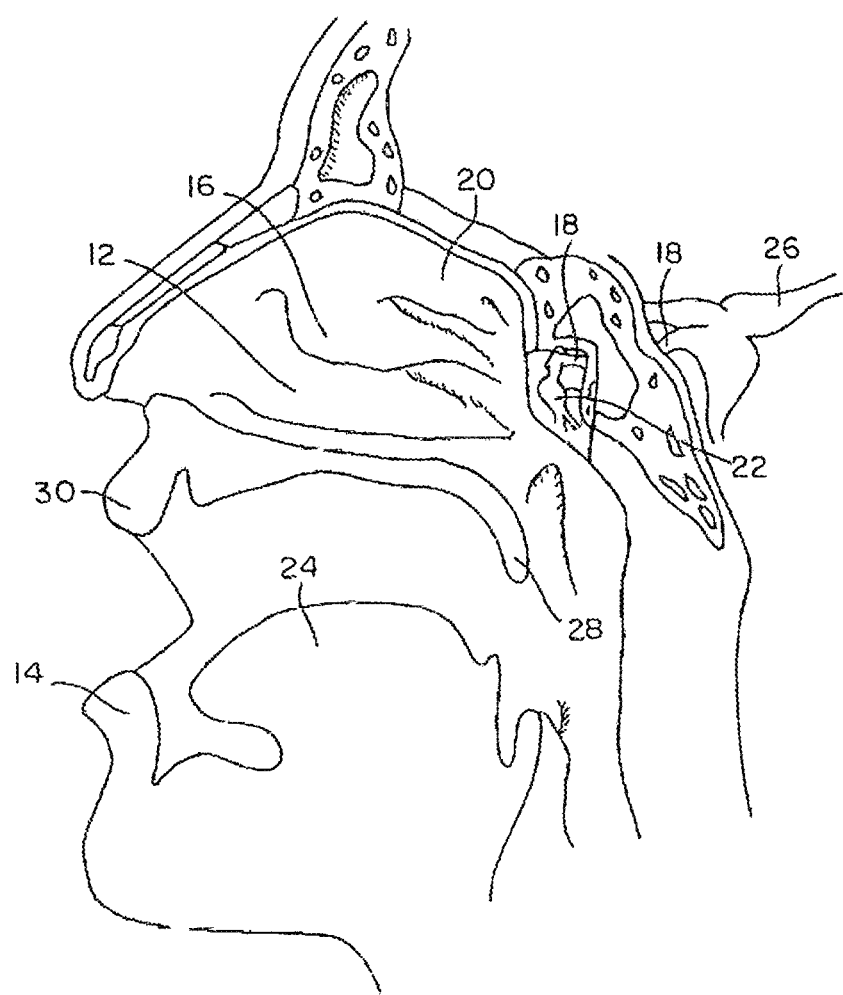
FIG. 1 is a diagram depicting a sagittal section of a portion of a human head, the section being just to the right of the nasal septum. A section is cut away at the posterior portion of the nasal cavity to reveal the approximate placement of the sphenopalatine ganglion. Indicia used in this Figure include 12 inferior concha, 14 lower lip, 16 middle concha, 18 maxillary nerve, 20 superior concha, 22 sphenopalatine ganglion, 24 tongue, 26 trigeminal nerve, 28 uvula, and 30 upper lip.
Figure 2:
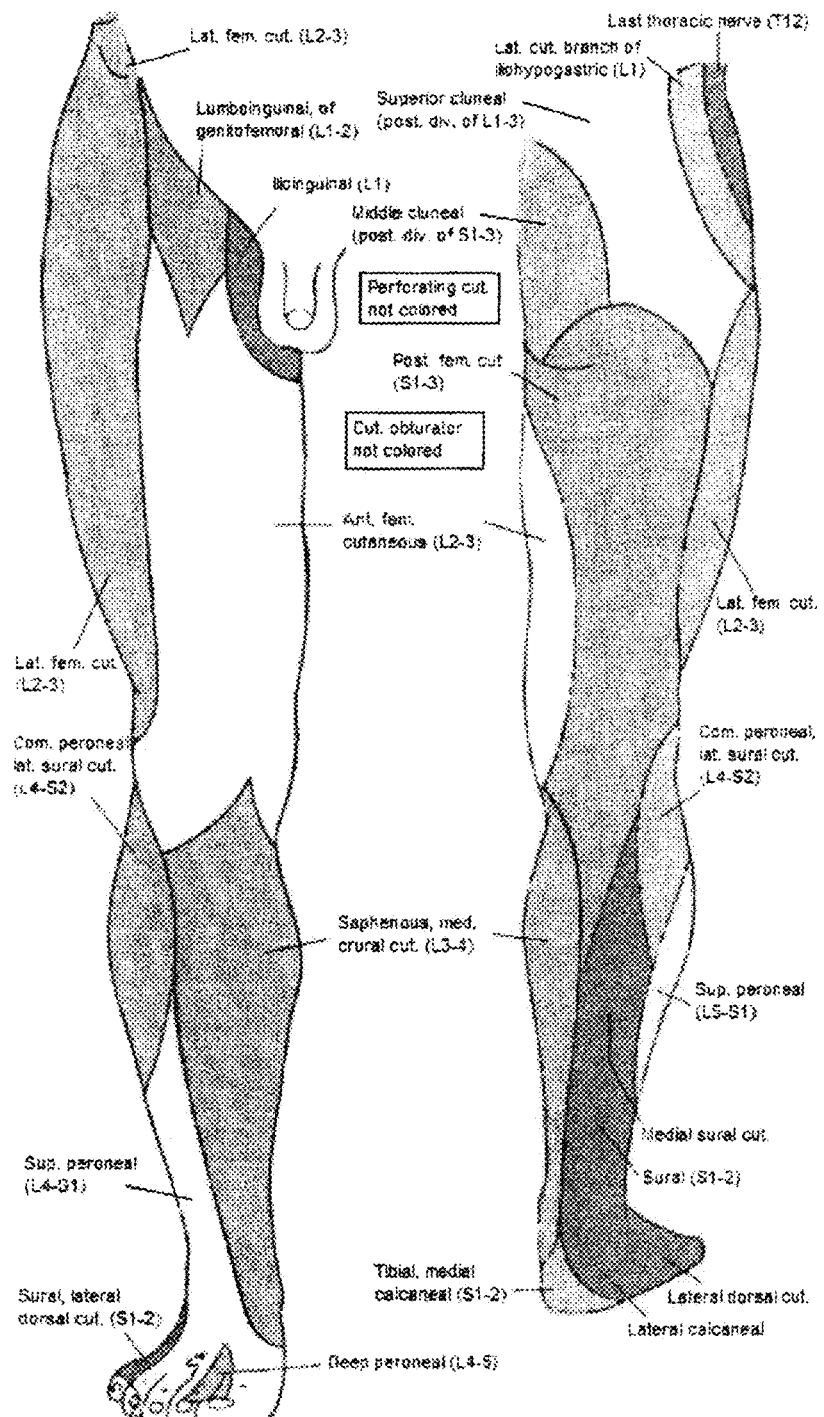
FIG. 2 is a self-explanatory illustration identifying nerves of a human leg that may be implicated in a disorder to be treated according to the present invention.
Figure 3:
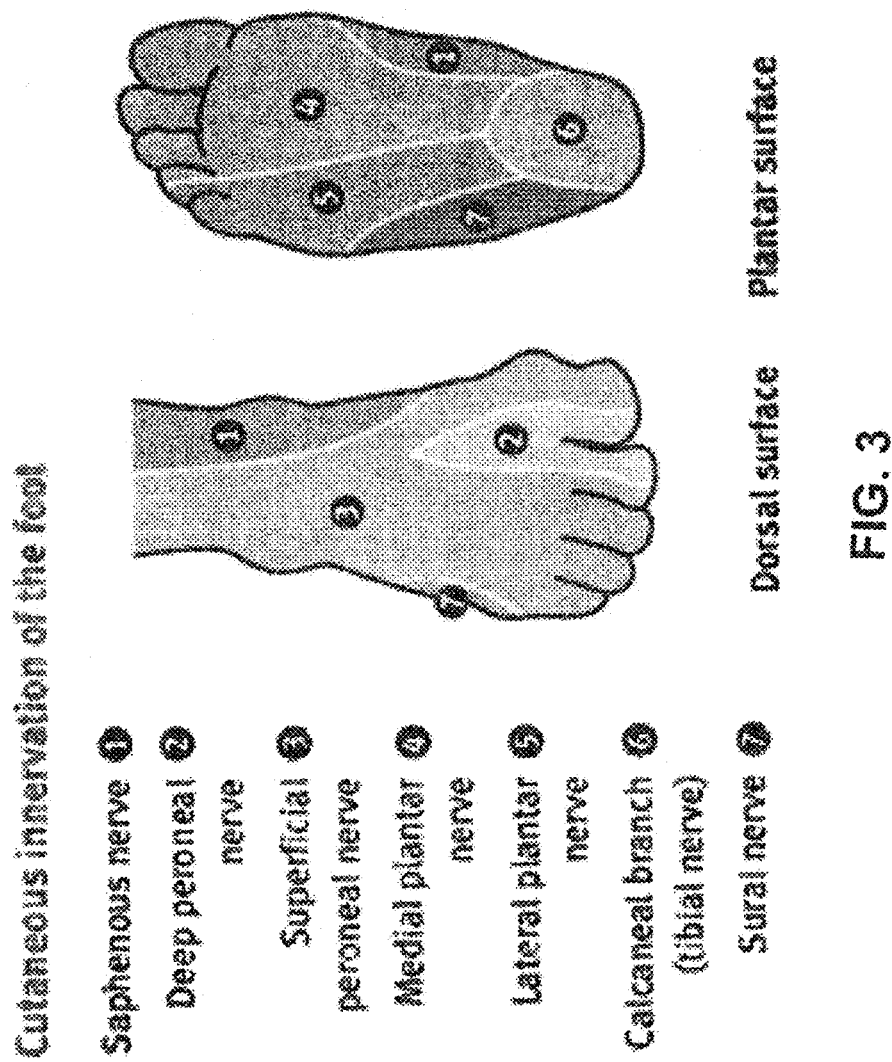
FIG. 3 is a self-explanatory illustration identifying nerves of a human foot that may be implicated in a disorder to be treated according to the present invention.

To treat pain, disease or suboptimal function involving any neurologic, intracranial, extracranial, nerve structure, spinal cord, cerebellar, pontine, Brainstem, basal ganglia, cranial nerve, or related structure, or peripheral nerve and particularly to treat of headache, cluster headache, migraine, facial pain, posttraumatic headache, Cervicogenic headache, occipital neuralgia, tinnitus, hearing or visual issues, postoperative or post surgical head, neck or facial pain, Post herpetic neuralgia or to enhance recovery from reconstructive, or other surgeries from trauma, Oncologic, or deformative pathologies or states, to improve cognitive function, treat PTSD, treat psychiatric disorders, vascular dementia, Alzheimer's disease symptoms or cognitive decline, control dangerous individuals or to keep them within or away from certain locations, improve sleep hygiene, improve wakefulness, decrease unwanted sequelae of sleep deprivation and in the treatment of dysesthesias or dental or oral pain including but not limited to burning mouth syndrome.

One aspect of the invention relates to a method of inhibiting a disorder in a human patient, the disorder comprising method of inhibiting a disorder in a human patient, the disorder comprising pain, or loss of motor or sensory function, sympathetic tone or range or fluidity of motion that is not cerebral neurovascular disorder pain or not muscular headache pain (hereinafter jointly referred to as "non-CNvD or muscular headache pain"), the method comprising affecting a nerve pathway at one or more locus associated with the disorder in a manner to inhibit the disorder to thereby inhibit the disorder, wherein at least one locus is a peripheral nerve structure physiologically or anatomically related to the nerve pathway that directly targets a Levin Sign or a Keystone nerve structure associated with the disorder. This method is effective in treating various injuries, trauma, post-surgical conditions, traumatic neuropathies and related disorders, including inhibiting pain associated with them, or for improving functionality following loss of motor or sensory function, sympathetic tone or range or fluidity of motion or trigeminal neuralgia or other disorder resulting from trauma, neoplasm, cancer, surgery, small fiber peripheral neuropathy or nerve damage or compromise, or sympathetic dysfunction involving the face, head, neck, back, oropharynx, oral, dental, temporomandibular joint or musculature (TMJ), thorax, abdomen, pelvis, genitalia, shoulder, back, elbow, wrist, fingers, hip, knee, ankle, toes or other joints, limbs or musculature or connective tissue or any combination of two or more of these disorders. This method comprises anesthetizing, blocking or disrupting at least at one locus a nerve structure, a small fiber branch or branches of one or more nerve structures or fibers involving sympathetic or parasympathetic one or more nerves that directly targets a Levin Sign or a Keystone nerve structure associated with the disorder to thereby inhibit the disorder. Any one or any combination of the Interventions could be used to do such anesthetizing, blocking or disrupting.

To treat pain, disease or suboptimal function involving any neurologic, intracranial, extracranial, nerve structure, spinal cord, cerebellar, pontine, Brainstem, basal ganglia, cranial nerve, or related structure, or peripheral nerve and particularly to treat of headache, cluster headache, migraine, facial pain, posttraumatic headache, Cervicogenic headache, occipital neuralgia, tinnitus, hearing or visual issues, postoperative or post surgical head, neck or facial pain, Post herpetic neuralgia or to enhance recovery from reconstructive, or other surgeries from trauma, Oncologic, or deformative pathologies or states, to improve cognitive function, treat PTSD, treat psychiatric disorders, vascular dementia, Alzheimer's disease symptoms or cognitive decline, control dangerous individuals or to keep them within or away from certain locations, improve sleep hygiene, improve wakefulness, decrease unwanted sequelae of sleep deprivation and in the treatment of dysesthesias or dental or oral pain including but not limited to burning mouth syndrome.

Another aspect of the invention is the combination of stimulation of SPG with branches of Trigeminal nerves, or occipital nerves. There is known C-2 and 3 connection with Trigeminal nerve and SPG and likely with C1. With injection of bupivacaine 0.5% to the Supratrochlear nerve, obtained better result with SPG block subsequently. With injection of occipital nerves with bupivicaine 0.5%, headache was further decreased with SPG block.

Another aspect is the combined dorsonasal neural structure including one or more of the SPG, the cavernous sinus ganglion, the carotid sinus ganglion, numerous branches of the maxillary nerve, the ethmoidal nerve, the ethmoidal ganglion, and the vidian nerve or other neural structure in close proximity of the SPG or sphenopalatine recess with stimulation of occipital nerve or sub occipital or high cervical segment including any of Cervical level (or proximal) 1-3 stimulation. Combined stimulation of a dorsonasal nerve with any one or more peripheral branches of the Trigeminal nerve or facial nerve including but not limited to one or more of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerve, anywhere in the course of the facial nerve from the intracranial or cisternal segment distally to the temporal, zygomatic, buccal, mandibular and cervical branches including efferent motor, parasympathetic or afferent sensory branches of the facial nerve. Also, combined occipital nerve, suboccipital, or high Cervical segment stimulation with any 1 or more branches of the Trigeminal nerve or facial nerve including but not limited to 1 or more of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerve, anywhere in the course of the facial nerve from the intracranial or cisternal segment distally to the temporal, zygomatic, buccal, mandibular and cervical branches including efferent motor, parasympathetic or afferent sensory branches of the facial nerve.

The invention also comprises stimulation of one or more loci of the facial nerve or components thereof, with one or more electrodes or stimulator device component. Stimulators may be implantable or non implantable.

Electrode or other stimulator device, magnet, heating device or component may be integral or detachable to a cap, hat, band, glass frame, mask, eye mask, sleep mask pillow, cushion or custom fit device apparatus for comfort and proper position. Optimal position may also be maximized by inflatable, temperature malleable or moldable bolsters or cushioning.

Multiple parameters may be independently adjusted for each stimulator locus including but not limited to timing of stimulation, synchronization or varied synchronization or nonsynchronization, waveform, frequency, amplitude, intensity, mode, directed stimulation and or signal propagation in anterograde or retrograde fashion or utilizing both in a manner including varied timing and parameters of antero and retrograde stimulation. In certain cases sensing patterns of neuronal conduction and generating augmented or subtracted stimulator induced propagation to cancel or resonate or otherwise alter conduction wave phases can decrease pain or improve and strengthen neuronal transmission to improve cognition, memory, motor coordination, sensation, or other functionalities in the CNS, PNS, musculoskeletal, endocrine or other organ or system function.

3D or other neural mapping by XRay, MRI, CT, PET scan, ultrasound, or MR neurography will better elucidate neural anatomy, as well as the anatomy and 'geometry' surrounding or associated tissue and Boney structures and recesses to allow for improved formation, construction, and configuration of the stimulator or 1 or more components and optimize electrode or component placement and will facilitate better placement of electrode or stimulator lead. Mapping coverage of stimulation area, by noting geographic anatomic localization of stimulation paresthesia in healthy person, or in afflicted patient, will allow the map of stimulated area to be matched more closely with the patients pain map and will optimize placement results. This can be done during placement, or adjusted for patient subgroup populations. Having ultrasound, XRay, MRI, ultrasound, or other CT or other modality to identify the stim or component will allow optimal placement. Hence radio opacity, or electrode or other localization modalities is productive.

One size, shape, array or configuration of stimulator type cannot deliver optimum stimulation for a given patient. Thin wafer or micro thin conductive electrodes may optimize placement.

3D printing of electrode or stimulator utilizing patient imaging studies will allow optimal peri or para neural placement. The array can be in three planes rather than a single lead point which is 2 dimensional or even linear. Based on actual imaging, a form of peri neural partial, or incomplete, garment type array would be optimum. Alternatively, different size stimulator arrays can be used to allow optimal patient placement by subgroup. Similarly, different shaped array configurations may be beneficial for different subgroups, and these can be based on population anatomic subtypes.

Another aspect of the invention relates to a method for treating a neuropathy associated with a disorder in a human patient, the method comprising: applying pressure in an increasing manner by palpation to an area associated with the neuropathy to determine a Keystone nerve which is triggering and essential to the neuropathy; applying the pressure US 2016/0030408 A1 to determine a point of at least one of maximum discomfort or trigger of increased trophic symptoms or findings to identify a Levin Sign as a locus of initial intervention; and intervening to treat the neuropathy at the location of the Levin Sign by one or more of foregoing Interventions, preferably by administration of a pharmaceutically active agent, internal implanted neurostimulation or external neurostimulation affecting a nerve pathway associated with the neuropathy in a manner to inhibit the neuropathy to thereby inhibit the neuropathy.

The foregoing methods of inhibiting such a disorder having non-CNvD or muscular headache pain, may relate to treatment of pain by anesthetizing, blocking or disrupting any one or more of the peripheral neural structures, peripheral nerve branches of cranial nerves or any neural structures enervating a patient's face, head and/or neck; intracranial pain; cancer-related pain of any one or more of the patient's face, head and/or neck; traumatic pain of any one or more of the patient's face, head and neck; trigeminal neuralgia; oral pain or dental pain; and any combination of two or more of these or the previously mentioned other disorders.

Another aspect of the invention relates to a device for stimulating, sensing a condition of or monitoring the function of an organ or tissue or for inhibiting a disorder in a human patient, the disorder comprising pain, or loss of motor or sensory function, sympathetic tone or range or fluidity of motion that is not cerebral neurovascular disorder pain or muscular headache pain, the device comprising an implantable or external stimulus, sensor or monitor component capable of stimulating, sensing a condition of or monitoring the function of the organ or tissue or affecting a nerve pathway associated with the disorder in a manner to enhance or sense the condition or function of the organ or tissue, or to monitor the function or to inhibit the disorder to thereby inhibit the disorder, the device further comprising a power source directly or indirectly coupled with the stimulus, sensor or monitor component to provide power to the stimulus, sensor or monitor component.

Another aspect of the invention relates to a method for stimulating, sensing a condition of or monitoring the function of an organ or tissue or for inhibiting a disorder in a human patient, the disorder comprising pain, or loss of motor or sensory function, sympathetic tone or range or fluidity of motion that is not cerebral neurovascular disorder pain or muscular headache pain, the method comprising stimulating, sensing a condition of or monitoring the function of the organ or tissue or affecting a nerve pathway associated with the disorder in a manner to enhance or sense the condition or function of the organ or tissue, or to monitor the function or to inhibit the disorder to thereby inhibit the disorder.

One method comprises intranasally administering a local anesthetic or local anesthetic pharmaceutical composition to a patient having non-CNvD or muscular headache pain in an amount effective to inhibit the pain or other symptoms of any of the disorders. According to this method, the local anesthetic pharmaceutical composition comprises a pharmaceutically acceptable carrier, at least one local anesthetic ingredient selected from the group consisting of a local anesthetic, a sustained release formulation of a local anesthetic or any effective medicament or compound and/or a compound selected from the group consisting of an antiepileptic, phenytoin sodium, a benzodiazepam, ion, membrane stabilizing agent, a serotonin receptor agonist, a serotonin subclass 5HT1F receptor agonist, LY334,370, a sesquiterpene lactone, parthanolide, *Tanacetum parthenium*, an extract of *Tanacetum parthenium*, anti neuropathic medication, gabapentin, pregabalin, duloxetine HCl, tricyclic or other antidepressant, amphetamine, ADHD medication, eszopiclone, muscle relaxant, zolpidem, sleeping agent, or cannabinoid agent.

Another aspect of the invention comprises anesthetizing a nerve structure, associated with the non-CNvD or muscular headache pain in the patient for a period effective to inhibit the pain. The nerve structure can be anesthetized by any method known in the art or described herein.

The nerve structure may be anesthetized, for example, by administering a local anesthetic pharmaceutical composition to the nerve structure or by performing acupuncture upon the nerve structure, or by surgically intervening to disrupt or sever the nerve structure, or by any of the Stimulation Techniques.

In one embodiment, the non-CNvD or muscular headache pain in a human patient is inhibited in the patient by energizing an electronic neural stimulator implanted in the patient in an area sufficiently adjacent to the nerve structure to disrupt the transmission of pain impulses locally or distally or in a manner which will alter sympathetic or parasympathetic neural impulse and/or tone or improve blood flow to the painful area or otherwise alter the perception of pain or other symptoms whether or not the nerve is blocked.

In another embodiment, the invention relates to a method of inhibiting non-CNvD or muscular headache pain in a human patient, the method comprising implanting an electronic neural stimulator in patient tissue adjacent a nerve structure responsible for affecting the pain and energizing the implanted electronic neural stimulator, so as to inhibit the non-CNvD or muscular headache pain.

In one embodiment, the nerve structure is a nerve of the head or neck or a dorsonasal nerve structure.

In one embodiment, the dorsonasal nerve structure is a trigeminal nerve or branch thereof.

In another embodiment, the dorsonasal nerve structure is a SPG or branch thereof.

In the Stimulation Techniques embodiments where an electric potential or electromagnetic radiation is applied by an implanted electronic neural stimulator, the method further comprises providing power to the implanted electronic neural stimulator using an external power supply, which optionally and preferably, is provided by inductively coupling the external power supply to the electronic neural stimulator.

The invention also relates to a kit comprising the local anesthetic or any other pharmaceutical composition as described herein and an intranasal drug delivery device or applicator for administering the composition to the patient. For example, the device or applicator may be one of those described in my U.S. Pat. Nos. 6,491,940, 7,799,337, that are or can be adapted for dorsonasal delivery to a specified nerve structure. The kit may also comprise instructional material which describes intranasal or dorsonasal administration of the composition to a human.

The invention also relates to a kit comprising devices to apply the Stimulation Techniques, including an external or internally implantable device that may have a power source or controller for the device that may be used extra-corporeally to activate, control, monitor or otherwise cause the implanted device to function, and instructional material which describes their use.

Another embodiment of the invention relates to peripheral nerve injections, stimulation, neuroaugmentation or neuromodulation involving a distinct nerve or ganglion structure which is targeted by the interventions. This embodiment targets peripheral nerve fibers or other structures physiologically or anatomically related to a given nerve structure, but without having to directly target the specific distinct nerve structure itself.

Another embodiment of the invention relates to combinations of techniques and/or locations and/or structures mentioned herein for treating the Disorders of Interest.

Another embodiment of the invention relates to treating the Disorders of Interest via stimulating the central nervous system, such as the spinal cord, in coordination with more peripheral stimulation, such as stimulating the median nerve for carpal tunnel syndrome.

Another embodiment of the invention relates to SPG stimulation with one or more peripheral nerve branches, such as the supratrochlear, lingual or facial nerve.

Another embodiment of the invention relates to blocking more than one peripheral nerve associated with the Disorders of Interest.

Another embodiment of the invention relates to variably programming any of the devices used in the Stimulating Techniques for treating the Disorders of Interest based on the relationship between two or more stimulation locations, involving different times of stimulation, varying amplitude, frequency or other parameters.

Another embodiment of the invention relates to using the Stimulation Techniques for treating the Disorders of Interest with implantations, or via topical means, such as including stimulating devices in a hat, or headband or a band around any other affected body part or tissue or a customized adhesive template to be used with one or more stimulator sites.

Another embodiment of the invention relates to treating the Disorders of Interest via drug infusion or delivery.

Another embodiment of the invention relates to a method that involves a direct, a fanlike or a regional distribution of neurostimulation of or administration of a pharmaceutical agent to small or peripheral nerve fibers associated with the nerve pathway.

Yet another embodiment of the invention relates to a method of treating complex regional pain syndrome of an upper extremity of a human patient, including or excluding the shoulder, the method comprising administering a local anesthetic agent in the vicinity of the patient's suprascapular nerve.

Still another embodiment of the invention relates to a method of treating complex regional pain syndrome of a lower extremity of a human patient, the method comprising administering a local anesthetic agent in the vicinity of a nerve of the lower extremities, such as, without limitation the patient's saphenous, tibial, posterior tibial or sural nerve.

Yet another embodiment of the invention relates to a method of treating complex regional pain syndrome relating to pain and decreased function of an arm or hand of a patient, the method comprising administering a local anesthetic agent in the vicinity of the patient's radial, medial, ulnar or musculocutaneous nerve.

Another embodiment of the invention relates to a method of treating at least one of facial pain, facial neuropathy, decreased eating function or decreased speech function of a patient, the method comprising administering a local anesthetic intranasally to the patient.

Yet another embodiment of the invention relates to a method of treating complex regional pain syndrome relating to shoulder, arm or hand of a patient, the method comprising directly injecting a local anesthetic and a steroid medication in the patient's suprascapular nerve along with administration of a local anesthetic and a steroid medication in the vicinity of the patient's suprascapular nerve.

Still another embodiment of the invention relates to a method of treating pain of facial trauma of a patient, the method comprising neurostimulation of the patient's sphenopalatine ganglion.

Another embodiment of the invention relates to a method of treating pain of trigeminal neuralgia of a patient, the method comprising stimulating the patient's sphenopalatine ganglion.

Yet another embodiment of the invention relates to a method of improving a human patient's shoulder's range of motion following injury, trauma, surgery, or frozen shoulder syndrome, the method comprising applying a local anesthetic or an anti-neuropathic agent in the vicinity of the patient's suprascapular nerve.

Still another embodiment of the invention relates to a method of improving a human patient's shoulder's range of motion following injury, trauma, surgery, or frozen shoulder syndrome, the method comprising applying a Stimulation Technique in the vicinity of the patient's suprascapular nerve.

DEFINITIONS

The following definitions, as well as other definitions set forth herein, apply to the terms used in the written description and/or the claims of this application.

As used herein, the term "cerebral neurovascular disorder" (CNvD) means a disorder which is characterized by one or more disturbances in the normal functioning of at least one component of the cerebral vascular or cerebral nervous system in a human. CNvDs which have been characterized include migraine, cluster headaches, other headaches of neurovascular etiology, tinnitus, and cerebrovascular spasm. An "acute" CNvD means an individual episode of a CNvD. Thus, an acute CNvD includes, but is not limited to, an acute neurovascular headache episode, a single episode of tinnitus, a single episode of cerebrovascular spasm, and a set of symptoms or a disorder manifested during or after and associated with an acute ischemic event such as a single cerebrovascular occlusion or a stroke. Accordingly, as used herein, the term "non-CNvD pain" as in the term "non-CNvD or muscular headache pain" or their equivalents means pain or symptoms associated with conditions or indications other than CNvDs or muscular headaches.

As used herein, cephalic inflammation includes, but is not limited to, cerebral inflammation, meningeal inflammation, and other varieties of extracranial and intracranial inflammation.

As used herein, any of the Disorders of Interest is "inhibited" if at least one symptom of an episode of any of the Disorders of Interest is alleviated, ameliorated, terminated, or prevented. As used herein, any of the Disorders of Interest is also "inhibited" if the frequency of recurrence, the severity, or both, of any of the Disorders of Interest is reduced.

As used herein, any of the Disorders of Interest is "terminated" if at least one symptom of any of the Disorders of Interest ceases in a patient and the patient does not experience the symptom for at least several hours or, preferably, for at least about one day.

As used herein, a "recurring" pain that is associated with any of the Disorders of Interest is pain which is experienced by a patient more than once in a six-month period.

As used herein, "acute pain" associated with any of the Disorders of Interest means a single pain episode which either has a duration about one hour or less in a human patient.

As used herein, the term "chronic pain" associated with any of the Disorders of Interest means pain which is experienced by a human patient more than fifteen days per month for a period of at least about six months.

As used herein, the teen "persistent pain" associated with any of the Disorders of Interest means pain which persists for a period longer than about one hour in a human patient.

As used herein, the term "recurrent pain" associated with any of the Disorders of Interest means pain which is experienced by a human patient more than once in a one-day period.

As used herein, the term "rebound" of pain associated with any of the Disorders of Interest means pain experienced by a patient or one or more symptoms of the pain following a period during which the patient did not experience the one or more symptoms, the symptom-free period having been preceded by an earlier period during which the patient experienced one or more symptoms associated with any of the Disorders of Interest. It is understood that it is not always possible to discern whether a patient who did not experience the one or more symptoms for a period is afflicted with the same episode or with a separate episode of the same pain associated with any of the Disorders of Interest. Thus, the term is inclusive of both situations.

As used herein, the term "prodromal symptom" associated with any of the Disorders of Interest means a symptom which is experienced by a patient and which is associated with the onset or indicates the imminent onset of an acute episode associated with any of the Disorders of Interest.

As used herein, a "nerve pathway" means a nerve structure or any one or more direct or indirect branches thereof or any tissue anatomically or physiologically associated with a nerve structure that affects the ability of the nerve structure to transmit pain or nerve impulses to affect a disorder associated with the nerve pathway.

As used herein, a "nerve structure" means a nerve, a plurality of nerves located in close anatomic proximity to one another, a ganglion, a nerve bundle or small nerve fibers.

As used herein, a nerve pathway or nerve structure is "associated with" any of the disorders of Interest if, when the nerve pathway or nerve structure is anesthetized in a human patient afflicted with any of the Disorders of Interest, the patient experiences relief from at least one symptom of any of the Disorders of Interest, whereby any of such Disorders of Interest is inhibited.

As used herein, a component of a device is "associated with" another component of the device or an accessory, dressing, artificial joint, appliance or the like, or a device is "associated with" another device, accessory, dressing, artificial joint, appliance or the like when the component or the device is on, within, integral to, attached to or remotely controls or is remotely controlled by the other component, device, accessory, dressing, artificial joint, appliance or the like.

As used herein, a "dorsonasal nerve structure" (DnNS) means the sphenopalatine ganglion (SPG) or a nerve structure located in close anatomic proximity to the SPG, as well as any of trigeminal nerve, trigeminal ganglion, cavernous sinus ganglion, carotic sinus ganglion, maxillary nerve, ethmoidal nerve, ethmoidal ganglion, and the vidian nerve, and any branch thereof.

As used herein, a "nerve of the head and neck" includes any one or combination of the following nerves, and any branch thereof: airiculotemporal, temporal, supraorbital, supratroclear, intraorbital, mental, stemocleidomastoid, great auricular, transverse cervical, supraclavicular, anterior primary rami, posterior primary rami, occipital, greater occipital and lesser occipital.

As used herein a "nerve of a lower extremity" includes any one or combination of the following nerves, and any branch thereof: femoral, lateral femoral cutaneous, lumboinguinal, genitofemoral, ilioinguinal, anterior femoral cutaneous, posterior femoral cutaneous, superior cluneal, medial cluneal, saphenous, tibial, posterior tibial, interosseous, sural, lateral sural cutaneous, medial sural cutaneous, lateral dorsal cutaneous, medial crural cutaneous, calcaneal, lateral calcaneal, common peroneal, superficial peroneal, deep peroneal, medial plantar and lateral plantar.

As used herein, a first nerve structure or a Stimulation Device is located in "close anatomic proximity" to a second nerve structure if the second nerve structure is affected following application of electronic or other stimulation of the first nerve structure or is affected by administration of a local anesthetic to a tissue which comprises or overlies the first nerve structure. For example, it is believed that dorsonasal administration of a local anesthetic or applying an electrical potential or electromagnetic radiation in close anatomic proximity to the nerve structure anesthetizes at least one, and perhaps all, of the SPG, the trigeminal nerve, the trigeminal ganglion, the cavernous sinus ganglion, the carotic sinus ganglion, numerous branches of the maxillary nerve, the ethmoidal nerve, the ethmoidal ganglion, and the vidian nerve. Thus, by way of example, each of the cavernous sinus ganglion, the carotic sinus ganglion, numerous branches of the maxillary nerve, the ethmoidal nerve, the ethmoidal ganglion, and the vidian nerve is located in close anatomic proximity to the SPG, and thus each is a DnNS.

As used herein, an "intranasal nerve structure" ("InNS") is a nerve structure that contacts the nasal epithelium or lies in sufficiently close proximity to the nasal epithelium that a compound applied to the epithelium is able to diffuse to or otherwise gain access to the nerve structure.

As used herein, an "intranasal blood vessel" ("InBV") is a blood or lymphatic vessel that contacts the nasal epithelium or lies in sufficiently close proximity to the nasal epithelium that a compound applied to the epithelium is able to diffuse to or otherwise gain access to the blood vessel.

As used herein, a nerve structure is "anesthetized" when the capacity of the nerve structure to generate or conduct nerve impulses is significantly impaired, relative to the capacity of the nerve structure to generate or conduct nerve impulses in the absence of intervention, such as by administration of a local anesthetic. Anesthesia of the SPG or the trigeminal nerve effected by administration of a local anesthetic, for example, interrupts the functioning normally associated with the SPG, the trigeminal nerve and with other DnNSs. It is understood that anesthesia of a nerve structure may be achieved not only using a local anesthetic, but also by any of the Interventions as set forth herein.

As used herein, the capacity of a DnNS to generate or conduct nerve impulses is "significantly impaired" when that capacity is reduced by an amount sufficient to inhibit the non-CNvD or muscular headache pain.

As used herein, the term "intranasal administration" of a composition and grammatical forms thereof mean delivery of the composition to any portion of the nasal epithelium.

As used herein, the term "dorsonasal administration" of a composition and grammatical forms thereof mean delivery of the composition to a tissue, fluid, or surface of a human, whereby a component of the composition is provided to a DnNS or to a tissue overlying a DnNS. Dorsonasal administration may be accomplished, for example, by topical administration of the composition to the region of the nasal epithelium overlying the SPG or to the surface of the nasal epithelium near the region of the nasal epithelium overlying the SPG, whereby a component of the composition is capable of diffusing through any tissue or fluid which may be interposed between the surface and the SPG. Such administration may also be accomplished, for example, by injecting the composition directly into the SPG or by injecting the composition into or otherwise administering the composition to a tissue or fluid near the SPG, whereby a component of the composition is capable of diffusing through any tissue or fluid which may be interposed between the site of injection or administration and the SPG.

As used herein, the term "the region of the nasal epithelium overlying the SPG" means the area of the nasal epithelium having a geometrical relationship with the SPG whereby an imaginary line approximately perpendicular to the surface of the epithelium and extending from the surface of the epithelium in the direction of the basement membrane of the epithelium passes through a DnNS.

As used herein, the term "the surface of the nasal epithelium near the region of the nasal epithelium overlying the SPG" means a portion of the surface of the nasal epithelium which is continuous with and sufficiently geometrically close to the region of the nasal epithelium overlying the SPG such that a compound applied anywhere on this surface is able to diffuse to the SPG. It is understood that the boundaries of the surface are dependent upon the diffusivity of the compound in the epithelium and in any tissue or fluid situated between the epithelium and the SPG. Thus, the area of this surface will be greater for a compound having high diffusivity than the area corresponding to a compound having a lower diffusivity. It is further understood that, where the compound has a half-life in vivo, the boundaries of "the surface of the nasal epithelium near the region of the epithelium overlying the SPG" are dependent upon the half-life of the compound. Thus, the area of this surface will be greater for a compound having a longer half-life than the area corresponding to a compound having a shorter half-life.

In the case of a compound having a diffusivity and a half-life comparable to that of ropivacaine, "the surface of the nasal epithelium near the region of the epithelium overlying the SPG" includes, but is not limited to, the surface of the region of the nasal epithelium overlying the SPG and the surface of the nasal epithelium continuous with and located within about three centimeters of that region. Preferably, such a compound is delivered to the surface of the nasal epithelium within about two centimeters of that region, and even more preferably to the surface of the nasal epithelium within about one centimeter of that region. Most preferably, the compound is delivered to the surface of the nasal epithelium overlying the SPG. It is understood that, in the case of a local anesthetic such as ropivacaine, the surface includes the epithelial surface covering the dorsal surface of the nasal cavity extending caudally from approximately the superior extent of the sphenoethmoidal recess to approximately the inferior boundary of the nasopharynx and extending laterally between the region of the surface covering the perpendicular plate of the right palatine bone and the region of the surface covering the perpendicular plate of the ethmoid bone and between the region of the surface covering the perpendicular plate of the left palatine bone and the region of the surface covering the perpendicular plate of the ethmoid bone.

As used herein, the "superior portion" of the nasal epithelium means one or more areas of the nasal epithelium situated on or above the superior face of the superior conchae.

As used herein, the term "non-intravenous administration" of a composition means administration of the composition by any means other than injection or infusion of the composition directly into the bloodstream of a human patient.

As used herein, the term "pharmaceutically acceptable carrier" means a chemical composition with which a local anesthetic may be combined and which, following the combination, can be used to administer the local anesthetic to a human patient without significantly adversely affecting the patient.

As used herein, "a sustained release formulation of a local anesthetic" is a pharmaceutical composition comprising a local anesthetic, wherein upon administration of the composition to a tissue of a human patient, the local anesthetic is delivered to the tissue on a continuous or semicontinuous basis for a period of hours, days, or weeks. Methods of making and using sustained release formulations of local anesthetics or other pharmaceutical compositions are well within the skill of one of ordinary skill in the art of pharmacology. In addition, inclusion of a vasoconstrictor in the composition may prolong the duration of the anesthetic effect.

As used herein, a composition is "formulated for intranasal delivery" if the composition is susceptible of intranasal administration to a human and if the composition is not significantly injurious to the tissues lining the nasal cavity of a human.

As used herein, the term "pharmaceutically active agent" means a compound or composition which, when administered to a human patient, has a biochemical or physiological effect on the patient.

As used herein, "instructional material" includes a publication, a sound, video, or other recording, a diagram, or any other medium of expression which can be used to communicate the usefulness of any pharmaceutically active agent or neurostimulation of the invention for inhibiting non-CNvD or muscular headache pain. The instructional material of the kit of the invention may, for example, be separate from, included with, or affixed to a container which contains the composition of the invention or be shipped together with a container which contains the composition or device used for neurostimulation. The instructional material may, for example, describe an appropriate dose of the composition of the invention or directions for using an applicator included in the kit to intranasally or dorsonasally administer a local anesthetic, or the use, operation, remote activation of or the like relating to any device applying an electrical potential or electromagnetic radiation to or otherwise stimulating the nerve structure.

As used herein, a "eutectic mixture" is a mixture comprising at least one local anesthetic and at least one eutectic ingredient.

As used herein, a "eutectic ingredient" is a chemical compound which, when mixed with a local anesthetic, yields a mixture having a melting point lower than the melting point of the local anesthetic.

As used herein, the term "comprise" or grammatical equivalents such as "comprises" or "comprising," means inclusion of a stated integer, part, component or step or group of integers, parts, components or steps, but not the exclusion of any other integer or step or group of integers or steps.

DETAILED DESCRIPTION OF EMBODIMENTS OF THE INVENTION

Treatment Involving at Least One Locus Associated with a LA Disorder

One aspect or embodiment of the present invention is a method of inhibiting a disorder in a human patient, the disorder comprising pain, or loss of motor or sensory function, sympathetic tone or range or fluidity of motion that is non-cerebral neurovascular disorder or muscular headache pain, the method comprising affecting a nerve pathway at one or more locus associated with the disorder in a manner to inhibit the disorder to thereby inhibit the disorder, wherein at least one locus is a peripheral nerve structure physiologically or anatomically related to the nerve pathway that directly targets a Levin Sign or a Keystone nerve structure associated with the disorder.

Such a disorder preferably includes posttraumatic or postsurgical pain; cancer-related pain, peripheral neuropathy, trigeminal neuralgia, or loss of motor or sensory function, sympathetic tone or range or fluidity of motion of any one or more of the patient's face, head, neck, oropharynx, oral cavity, dental structure, temporomandibular joint or musculature, thorax, abdomen, pelvis, genitalia, joint, limb, musculature or connective tissue, and any combination of two or more of these disorders.

Other preferred Disorders of Interest treated by this method include CRPS types I and II, as well as frozen shoulder syndrome, restriction of shoulder range of motion following trauma, injury or surgery or sympathetic mediated disorder, post-surgical cervical, thoracic or lumbar pathology, pain or other symptoms following spinal fusion or laminectomy, spinal or joint degenerative disease or trauma.

Preferably, the primary or initial locus of the loci that are sites of any Intervention used to treat such disorders by this method is a peripheral nerve structure physiologically or anatomically related to the nerve pathway that directly targets a Levin Sign or a Keystone nerve structure associated with the disorder. At least one other locus is a peripheral nerve structure physiologically or anatomically related to the nerve pathway that does not directly target a Levin Sign or a Keystone nerve structure associated with the disorder, but nevertheless is significantly associated with the disorder. Preferably, more than one locus associated with the disorder is affected.

Preferred nerve pathways to be treated are at least one of a nerve structure involving a suprascapular nerve or small fibers therein; a sympathetic or parasympathetic neural structure that is not directly located in the central nervous system; or stellate, lumbar paravertebral or other ganglia; a paraspinal branch of a neural structure; paraspinal sympathetic or parasympathetic fibers not in ganglion structures; a radicular nerve; or a small fiber or sympathetic or parasympathetic neural structure related to a major peripheral nerve. Other preferred nerve pathways to be treated are at least one of a suprascapular, radial, ulnar, median, musculocutaneous, a nerve of the lower extremities, such as tibial, peroneal, sural, saphenous or a nerve of the head and neck, such as a peripheral facial nerve.

Any one or any combination of the Interventions may be used to treat the locus or loci according to this embodiment of the invention, including but not limited to a one or more of a direct, a fanlike or a regional distribution of application of a Stimulation Technique to or administration of a pharmaceutical agent to small or peripheral nerve fibers associated with the nerve pathway.

Identification of Treatment Site Involving a Keystone Nerve and Levin Sign

Another aspect of the present invention relates to a method for treating a neuropathy associated with a disorder in a human patient, the method comprising: applying pressure in an increasing manner by palpation to an area associated with the neuropathy to determine a Keystone nerve which is triggering and essential to the neuropathy; applying the pressure to determine a point of at least one of maximum discomfort or trigger of increased trophic symptoms or findings to identify a Levin Sign as a locus of initial intervention; and intervening to treat the neuropathy at the location of the Levin Sign by one or more of foregoing Interventions, preferably by administration of a pharmaceutically active agent, internal implanted neurostimulation or external neurostimulation affecting a nerve pathway associated with the neuropathy in a manner to inhibit the neuropathy to thereby inhibit the neuropathy.

In this method, the neuropathy preferably includes but is not limited to neuropathy associated with a disorder selected from the group consisting of posttraumatic or postsurgical pain; cancer-related pain, peripheral neuropathy, trigeminal neuralgia, or loss of motor or sensory function, sympathetic tone or range or fluidity of motion of any one or more of the patient's face, head, neck, oropharynx, oral cavity, dental structure, temporomandibular joint or musculature, thorax, abdomen, pelvis, genitalia, joint, limb, musculature or connective tissue, such as tendons or ligaments, or any combination of two or more of the disorders.

Non-limiting, preferred disorders to be treated are those mentioned above regarding the treatment involving at least one, and preferably, at least two loci, as are the nerve pathways and nerve structures, so they will not be repeated here. Likewise, any of the Interventions may be used to treat the neuropathies or disorders identified using the Keystone Nerve and Levin Sign.

Interventions

As noted in the Background of the Invention section above, many different types of interventions may be used to treat the disorders, neuopathies, indications, conditions and symptoms according to the present invention. Any single one or any combination of the disorders, neuropathies, indications, conditions and symptoms are treated according to this invention by affecting, such as by anesthetizing, blocking or disrupting a nerve pathway associated with the neuropathy, pain, disorder or dysfunction, such as but not limited to a dorsonasal nerve structure, a nerve of the head and neck, a nerve of the lower extremities, any portion of the spinal cord, surprascapular nerve, radial nerve, median nerve, ulnar nerve, musculocutaneous nerve, or peripheral or sympathetic nerves, including branches and small fibers of such nerves, associated with the neuropathy, pain, disorder or dysfunction in any manner to inhibit the neuropathy, pain, disorder or dysfunction. The nerve pathway may be anesthetized, blocked or disrupted by any of the following interventions: (a) performing acupuncture upon the nerve structure; (b) surgically intervening to disrupt or sever nerve structures; (c) by applying a Stimulation Technique or using a Stimulation Device as defined above, or (d) administering by any suitable means, such as parenterally, topically, transcutaneously, intranasally or dorsonasally, a local anesthetic or other pharmaceutically active agent capable of anesthetizing, blocking or disrupting any of the foregoing disorders, alone or together, to the area or areas containing or affecting the nerve pathway.

Acupuncture and surgical interventions are well known to those of ordinary skill in the art of medical treatments and therefore, need not be disclosed in detail. The significant aspect of applying these interventions is identifying the site or sites associated with the disorders, neuropathies, indications, conditions and symptoms. The identification of the Keystone nerve and Levin Sign as discussed above is the preferred way to determine the site or sites of these interventions.

Stimulation Techniques include applying an electrical potential or current, including low level current, or electromagnetic radiation to the nerve pathway externally or internally, such as transepithelial (also known as transcutaneous) electrical neural stimulation or by implantable and preferably a miniaturized electronic stimulation device or energy generating device stimulator such as microelectromechanical systems (MEMS), nanoelectromechanical systems (NEMS), magnetic induction, radio frequency radiation or visible or non-visible light frequency, x-rays, proton bombardment, ultrasound, infrasound, near infrared or laser, applying heat, applying cold, mechanical massage; or any other technique for stimulating an organ, tissue or nerve pathway to inhibit the disorder, neuropathy, indication, condition or symptom or to sense a condition of or monitor a function of an organ, tissue or nerve pathway, or for any other purpose set forth herein.

The disorders, etc., treated by the Stimulation Technique and the nerve pathways and nerve structures so treated are those described above regarding the treatment involving at least one locus, and will not be repeated here in detail.

There are many Stimulation Techniques well known to those of ordinary skill in the art, so a detailed description of them will not be presented here. A key aspect is determining which nerve pathway or pathways is or are involved. The method involving the Keystone nerve and Levin Sign is the preferred method, but any other method known to those skilled in the medical treatment art involving stimulation techniques would also be suitable.

Stimulation Techniques that could be applied after identifying the locus or loci of treatment could be to apply the stimulation in sufficient anatomic proximity to the Levin Sign associated with the nerve pathway so as to inhibit pain associated with the disorder. The stimulation could be applied internally within the patient's body or externally of the patient's body.

In addition to treating the disorders, neuopathies, indications, conditions and symptoms mentioned above, one or more Stimulation Device may be used to apply one or more Stimulation Technique to an organ or tissue to stimulate, sense the condition of and/or to monitor the function of an organ or tissue. The organ or tissue can be any organ or tissue that may be affected in a human, including replacement, artificial or prosthetic organs or tissues. Non-limiting examples are bones, joints, muscles, cartilage, tendons, ligaments, vasculature, heart, lungs, gastro-intestinal organs, or liver among others. Thus, the Stimulating Device or other stimulating, sensing or monitoring devices well known to those skilled in the art may be used for such diverse purposes by way of example without limitation, as stimulating bone growth electronically or otherwise, such as by drug emission including directed drug emission, determining whether infection is present, to sense or monitor conditions, such as temperature, pH, pK, oxygen, carbon dioxide, extent of replacement organ or tissue rejection, or to sense or monitor organ or tissue function such as directions and degrees of motion of natural or replacement joints, the status of joint components, or to regulate stem cell implant, or tissue growth parameters, for instance.

Another aspect of the invention relates to a device for stimulating, sensing a condition of or monitoring the function of an organ or tissue or for inhibiting a disorder in a human patient, the disorder comprising pain, or loss of motor or sensory function, sympathetic tone or range or fluidity of motion that is not cerebral neurovascular disorder pain or muscular headache pain, the device comprising an implantable or external stimulus, sensor or monitor component capable of stimulating, sensing a condition of or monitoring the function of the organ or tissue or affecting a nerve pathway associated with the disorder in a manner to enhance or sense the condition or function of the organ or tissue, or to monitor the function or to inhibit the disorder to thereby inhibit the disorder, the device further comprising a power source directly or indirectly coupled with the stimulus, sensor or monitor component to provide power to the stimulus, sensor or monitor component.

The device may be or comprise any one or combination of the foregoing Stimulation Devices, preferably external or transcutaneous or implantable electronic neural stimulators. For example without limitation, the implantable electronic neural stimulator may be a MEMS device, a NEMS device, a maxillofacial device, one or more implantable electrodes. Implantable and other types of electronic neural stimulators are available from companies like Autonomic Technologies, Inc., EP Global Communications, Inc. and its related company EPGL Medical, among many other sources.

The implantable electronic neural stimulator may have an internally implantable component for supplying at least one of power, control or monitoring to the stimulus, sensor or monitor component. The patient's living tissues in close anatomic proximity to the internally implanted stimulus, sensor or monitor component and to the internally implantable component may supply at least one of power and biofeedback for use in powering, controlling or monitoring the stimulus, sensor or monitor component. Alternatively, an internally implantable component for supplying at least one of power, control or monitoring to the stimulus, sensor or monitor component may be separately implantable in a location in the patient remote from the stimulus, sensor or monitor component.

Another alternative is that the electronic neural stimulator may include an external component for supplying at least one of power, control or monitoring to the stimulus, sensor or monitor component that remotely or inductively supplies power control or monitoring to the stimulus, sensor or monitor component of the implantable electronic neural stimulator.

Yet another alternative is that the device is an external electronic neural stimulator in sufficient anatomic proximity to a portion of the patient's body in the vicinity of the nerve pathway to be stimulated. In this instance, the external electronic neural stimulator may be, for example without limitation, a transepithelial neural stimulator, a needle electrode, a device associated with a brace, a device associated with a band, a device associated with headgear (such as a Cefaly® device available from Cefaly Technology, Herstal, Belgium), a device associated with an accessory wearable by the patient (such as an article of clothing like a shirt, blouse, pants, dress, skirt, sweater, jacket, hat, scarf, socks, stockings or shoes, for example; or worn like jewelry, such as a watch, bracelet or necklace for example). The Stimulator Device may be in the form of a device associated with a furnishing (such as a chair, sofa, bed, bolster or pillow in the vicinity of the nerve pathway to be stimulated, a device associated with an artificial or prosthetic joint, organ or tissue, a device associated with intra-medullary hardware, or a device associated with spinal or vertebral surgery hardware (such as fusion devices, fusion hardware, fusion plates, screws, or artificial or replacement discs or artificial or replacement vertebral bodies or spacers). Other non-limiting, exemplary devices that can be associated with MEMS or other Stimulation Devices that can also sense, monitor, modulate or otherwise affect an organ, tissue or nerve pathway include those associated with a bone stimulator or bionengineered discs or joints that can have an integral MEMS device that can monitor or modulate stem cell or other cellular growth via electronic, chemical or mechanical means.

Stimulation of the organ, tissue or nerve pathway can be done using any number of various types of stimulation. Non-limiting examples include one or more of applying an electrical potential or current, including low level current, or electromagnetic radiation, magnetic induction, radio frequency radiation or visible or non-visible light frequency, x-rays, proton bombardment, ultrasound, infrasound, near infrared or laser; application of heat, application of cold, or mechanical massage.

Spinal cord stimulation may be effected by one of more of single or strings of interconnected stimulators such as MEMs that can be implanted in or on the spinal cord, distal plexus, ganglion, plexus, peripheral nerves or small fiber nerves.

The stimulation techniques may include, for example without limitation, applying the stimulus to one or more than one distinct locus of stimulation. The electronic neural stimulus can be used with coordinated or non-coordinated variable parameters to optimize effect, such as one or more of time, amplitude, frequency, intensity, sequence, pulse or pulse width.

Intervention by Application of Pharmaceutically-Active Agent

Inhibition of the disorder, condition or indication may include administering by any suitable means, such as parenterally, topically, transcutaneously, intranasally or dorsonasally, a suitable pharmaceutically active agent capable of anesthetizing, blocking or disrupting any of the Disorders of Interest, alone or together, to the areas containing or affecting the nerve pathway.

One aspect of the present invention regarding intervention by a pharmaceutically-active agent is based on the discovery that intranasal administration of a local anesthetic pharmaceutical composition to a human patient experiencing non-CNvD or muscular headache pain inhibits the non-CNvD or muscular headache pain or one or more of its associated symptoms, such as those, for example, associated with traumatic or postsurgical neuropathy involving peripheral or other nerve fibers innervating the face, head, neck, oropharynx, oral cavity, dental structure or temporomandibular joint or musculature. The invention also relates to the discovery that anesthesia of a dorsonasal nerve structure (DnNS) or a nerve of the head and neck in a human patient experiencing Disorder of interest that is non-CNvD or muscular headache pain inhibits the non-CNvD or muscular headache pain or one or its associated symptoms involving the peripheral branches of nerves in the face, head, neck, oropharynx, oral cavity, dental structure or temporomandibular joint or musculature.

Local anesthetics are known to provide analgesia to a body surface to which they are applied. However, such analgesia persists only for a period of time which is characteristic of the particular local anesthetic used and the site anesthetized. Local anesthetics may be roughly divided into classes based on the duration of analgesia provided to a patient following topical administration.

It is known that intranasal administration of a relatively shorter-acting local anesthetics such as lidocaine or cocaine decreases head pain for a period approximately equal to the duration of analgesia which is characteristic of such shorter-acting local anesthetics. Lidocaine and cocaine each exhibit a duration of action shorter than about one hour when intranasally administered.

What was not known, and what represents a surprising discovery, is that intranasal, and preferably dorsonasal, administration of a local anesthetic preparation which relieves a symptom of the non-CNvD or muscular headache pain is effective both to relieve pain and related symptoms, such as dysesthesias, beyond the period of expected anesthesia and, more importantly, to inhibit the non-CNvD or muscular headache pain. It has furthermore been discovered that conditions associated with non-CNvD or muscular headache pain can be inhibited by interrupting or interfering with neural transmission of neural impulses through one or more DnNSs, such as by intranasally (and preferably dorsonasally) administering a local anesthetic pharmaceutical composition to the patient, by neurostimulating a nerve pathway associated with a Disorder of Interest, such as by applying an electrical potential or current to the nerve pathway, or by any other anesthetic method described herein.

Inhibition of Disorders of Interest

One aspect of the invention is based on the discovery that intranasal, and preferably dorsonasal administration of a local anesthetic pharmaceutical composition to a human patient experiencing any of the Disorders of Interest inhibits the any of the Disorders of Interest. The local anesthetic pharmaceutical composition comprises a local anesthetic ingredient.

Intranasal, and preferably dorsonasal, administration of at least one local anesthetic, such as bupivacaine or ropivacaine, to a human patient experiencing any of the Disorders of Interest is sufficient to inhibit the pain or a symptom of any of the Disorders of Interest. Furthermore, intranasal or dorsonasal administration of a composition comprising a sustained release formulation of a shorter-acting local anesthetic inhibits any of the Disorders of Interest or a symptom thereof. By way of example, any of the Disorders of Interest may be acute, persistent, chronic, recurring or recurrent.

Prior art methods of treating pain associated with any of the Disorders of Interest often transiently and/or incompletely relieve the pain, the primary symptom of many such disorders. In contrast, the methods, compositions, devices and kits of the present invention provide lasting and effective relief of the symptoms of pain associated with any of the Disorders of Interest. Without wishing to be bound by any particular theory, it is believed that intranasal administration of a local anesthetic pharmaceutical composition to a patient experiencing pain associated with any of the Disorders of Interest provides relief by inhibiting the physiological processes underlying the pain, whereby both the pain associated with any of the Disorders of Interest and its other associated symptoms are inhibited.

Prevention of Acute Pain Associated with any of the Disorders of Interest

The method described herein for inhibiting pain associated with any of the Disorders of Interest includes a method of preventing such pain, including a method of preventing one or more symptoms (e.g., inflammation) associated therewith. Certain pain associated with any of the Disorders of Interest is associated with prodromal symptoms which are experienced by a patient prior to the onset of the disorder. By treating a patient using the method described herein for inhibiting pain associated with any of the Disorders of Interest at a time when the pain is expected or at a time when a prodromal symptom of the pain is experienced by the patient, the pain associated with any of the Disorders of Interest may be prevented. Decreasing the Frequency and/or Severity of Recurring Disorders of Interest.

Numerous pains associated with any of the Disorders of Interest are characterized by periodic or irregular recurrence. Over time, severity of such pain often seems to increase and many afflicted patients seem to experience pain episodes more frequently. It was observed that the frequency of recurrence and severity of such pain episodes decreased with time in patients using the compositions and methods described in the present disclosure, even after treatment was no longer administered. These phenomena have not been previously observed with any other treatment method. The methods, compositions, devices and kits of the invention are useful for decreasing the frequency of recurrence, the severity, or both, of pain episodes experienced by a patient afflicted with associated Disorders of Interest.

The invention thus includes in one embodiment a method of decreasing the frequency or severity with which pain episodes associated with any of the Disorders of Interest are experienced by a patient afflicted with recurring pain associated with any of the Disorders of Interest. One embodiment of a method comprises intranasally, and preferably dorsonasally, administering to a patient experiencing a pain episode associated with any of the Disorders of Interest a local anesthetic pharmaceutically active agent or pharmaceutical composition. The composition comprises a local anesthetic or a sustained release formulation of a local anesthetic, and is preferably administered to the patient early in the course of the episode. Preferably, the local anesthetic is administered to the patient within two hours following the onset of the episode, more preferably within one hour, and even more preferably within thirty minutes of the onset. Early administration Provides more prompt relief, but administration of the local anesthetic according to this invention may be at any time with good results.

Inhibition of pain associated with any of the Disorders of Interest by application of a pharmaceutically active agent preferably involves administration that may be parenteral, topical, transcutaneous or otherwise, including intranasal, and preferably dorsonasal, administration of a pharmaceutically active agent, preferably a local anesthetic pharmaceutical composition which provides relief from a symptom of the disorder for a period of at least about one hour, and preferably at least about two hours.

Combining a local anesthetic pharmaceutical composition with another agent, including but not limited to neuropathic pain agents, antiseizure agents, antidepressants, ADHD, sleep medications, antiinflammatory agents, serotonin agonists or antagonists will have an additive, if not synergistic, effect on therapeutic efficacy because the disease process is inhibited by different mechanisms.

Local Anesthetics

The chemical identity of the local anesthetic or anesthetics used in the compositions and methods of the invention is not critical. As described herein, local anesthetics may be administered in pharmaceutically acceptable carriers, and in sustained release formulations or in conjunction with an additional compound which extends their anesthetic effect.

Compounds having local anesthetic activity which may be used to practice the invention include, but are not limited to, articaine, ambucaine, amolanone, amylocaine, benoxinate, betoxycaine, biphenamine, bupivacaine, levobupivacaine, butacaine, butamben, butanilicicaine, butethamine, butoxycaine, carticaine, 2-chloroprocaine, cocaethylene, cocaine, cyclomethycaine, dibucaine, dimethisoquin, dimethocaine, diperodon, dyclonine, ecgonidine, ecgonine, ethyl am inobenzoate, ethyl chloride, etidocaine, levo-etidocaine, dextro-etidocaine, beta-eucaine, euprocin, fenalcomine, fomocaine, hexylcaine, hydroxyprocaine, hydroxytetracaine, isobutyl p-aminobenzoate, leucinocaine mesylate, levoxadrol, lidocaine, lidocaine salicylatemonohydrate, meperidine, mepivacaine, levo-mepivacaine, meprylcaine, metabutoxycaine, methyl chloride, myrtecaine, naepaine, octacaine, orthocaine, oxethazaine, parethoxycaine, phenacaine, phenol, pipecoloxylidides, piperocaine, piridocaine, polidocanol, pramoxine, prilocaine, procaine, propanocaine, proparacaine, propipocaine, propoxycaine, pseudococaine, pyrrocaine, quinine urea, risocaine, ropivacaine, levo-ropivacaine, salicyl alcohol, sameridine, tetracaine, tolycaine, trimecaine, veratridine, and zolamine, as well as 2-alkyl-2-alkylamino-2',6-acetoxylidide compounds, such as those described in U.S. Pat. No. 3,862,321; glycerol 1,2-bis-aminoalkyl ether compounds, such as those described in U.S. Pat. No. 4,117,160; benzisoxazole compounds, such as those described in U.S. Pat. No. 4,217,349; 0-aminoalkyl-salicylate compounds, such as those described in U.S. Pat. No. 4,298,603; heterocyclic phenoxyamine compounds, such as those described in U.S. Pat. No. 4,379,161; 2- and 3-aryl substituted imidazo (1,2-A) pyridine compounds, such as those described in U.S. Pat. No. 4,871,745, in U.S. Pat. No. 4,833,149, and in U.S. Pat. No. 4,727,145; poly-organophosphazene compounds, such as those described in U.S. Pat. No. 4,495,174 and in U.S. Pat. No. 4,636,387; tertiary-alky-amino-lower acyl-xylidide compounds, such as those described in U.S. Pat. No. 3,925,469; amidinourea compounds, such as those described in U.S. Pat. No. 4,147,804; 3-(5'-adenylates) of lincomycin-type or clindamycin-type compounds, such as those described in U.S. Pat. No. 4,397,845; N-substituted derivatives of 1-(4'-alkylsulfo-nylphenyl)-2-amino-1,3-propanediol compounds, such as those described in U.S. Pat. No. 4,632,940; tertiary amino-alkoxyphenyl ether compounds, such as those described in U.S. Pat. No. 4,073,917; adenosine compounds, such as adenosine and adenosinemono-, di-, and triphosphate; lauryl polyglycol ether compounds, such as those described in U.S. Pat. No. 5,676,955 and mixtures of such ether compounds; 2-(omegaalkylaminoalkyl)-3-(4-substituted-benzylidene) phthalimidine compounds or 2-(omega-dialkylaminoalkyl)-3-(4-substituted-benzylidene) phthalimidine compounds, such as those described in U.S. Pat. No. 4,551,453; N,N,N-triethylN-alkyl ammonium salts, such as those described in U.S. Pat. No. 4,352,820; L-N-n-propylpipecolic acid-2,6-xylidide compounds, such as those described in U.S. Pat. No. 4,695,576; N-substituted 4-piperidinecarboxamide compounds, such as those described in U.S. Pat. No. 5,756,520; N-substituted 4-phenyl-4-piperidinecarboxamide compounds, such as those described in U.S. Pat. No. 5,360,805; polymers comprising repeating units of one or more local anesthetic moieties, such as polymers described in U.S. Pat. No. 3,914,283; compounds of formula (I) and its derivatives, such as those described in International Patent Application Publication No. WO 97/38675; compounds of formula (II) wherein $R_{1-4}$, m, and Pare defined as in International Patent Application Publication No. WO 95/21821; compounds having a structure described in International Patent Application Publication No. WO 97/15548; compounds having a structure described in International Patent Application Publication No. WO 97/23467; compounds having a structure described in U.S. Pat. No. 4,870,086; compounds having a structure described in U.S. Pat. No. 4,529,601; topical anesthetic agents; topical anesthetic products of Astra {AstraZeneca} of the "LTA" series of compounds; ester forms of any of these compounds, salts of any of these compounds, compounds otherwise chemically related to one of these compounds which would be effective in the present invention; and sustained release preparations of any of these agents, as described herein. Also included are derivatives of the foregoing, where the derivative is any chemically related compound effective for the present invention.

Synonyms, including chemical names, chemical formula, and trade names, for many of the local anesthetics described herein may be found in Physician's Desk Reference® (Medical Economics Co., Inc., Montvale, N.J., 51$^{st}$ ed., 1997) or in PDR® GENERICS™ (Medical Economics Co., Inc., Montvale, N.J., 2nd ed., 1996), or in later editions of these publications.

The local anesthetic is preferably selected from the group consisting of bupivacaine, levo-bupivacaine, ropivacaine, levo-ropivacaine, tetracaine, etidocaine, levo-etidocaine, dextro-etidocaine, and levo-mepivacaine.

Local anesthetics including, but not limited to, bupivacaine and ropivacaine, which are related to aminoacyl local anesthetics exhibit intrinsic vasoactive effects on cerebral blood vessel tone and reduce pain sensitivity locally. When administered dorsonasally, these compounds are believed to effect anesthesia of the SPG and other DnNSs, which results in increased volumetric flow of blood in cerebral blood vessels and reduces inflammation initiated by functional ischemia. It is understood that the S (levo)-enantiomer of ropivacaine and the S (levo)-enantiomer of bupivacaine exhibit lower physiological toxicity and better sensory blocking properties than the corresponding R (dextro)-enantiomers. The S (levo)-enantiomer of ropivacaine is preferred for use in the compositions and methods of the invention, as are the S (levo)-enantiomers of bupivacaine, etidocaine, and mepivacaine.

Ropivacaine exhibits lower cardiovascular and central nervous system toxicity than bupivacaine. Compared with bupivacaine, ropivacaine blocks nerve fibers, such as A (delta) and C sensory fibers, more preferentially than other neurons such as motor neurons (Rosenberg et al., 1986, Br. J. Anaesth. 55:163-167). Thus, ropivacaine is preferred over bupivacaine in the compositions, kits, and methods of the invention.

For local anesthetics which have a chiral center (e.g., bupivacaine and ropivacaine), the local anesthetic may be a single optical isomer of the local anesthetic, a racemic mixture of the optical isomers, or some other mixture of optical isomers. By way of example, a 90:10, a 80:20, a 75:25, a 70:30, or a 50:50 ratio, by weight or by molecule number, of one optical isomer to the other may be used. There is clinical evidence that mixtures of local anesthetics such as bupivacaine and ropivacaine, wherein about 10-25% of the anesthetic is present in the dextro-form can provide anesthesia of longer duration, more pronounced anesthetic effect, or both.

When the local anesthetic is an alkyl- or aryl-2-piperidinecarboxamide derivative such as mepivacaine, bupivacaine, ropivacaine, or etidocaine, the carbon atom at position 2 of the piperidine ring is a chiral center, as indicated with an asterisk in formula (III), wherein R is ethyl, phenyl, or C5-C8 straight- or branched-chain alkyl, and R' is 2,6-dimethylphenyl, thiophene, or 2,5-dimethylthiophene.

For these local anesthetics, it is preferred by the inventor to use the levo-enantiomer at this chiral center in the compositions, kits, apparatus, and methods of the invention.

Similarly, when the local anesthetic comprises a chiral center (indicated with an asterisk) having the structure of formula (IV), it is also preferred that the levo-enantiomer at the chiral center be used in the compositions, kits, and methods of the invention, wherein R and R' are as defined above and wherein either (i) each of R" and R''' is a straight-chain alkyl and R" and R''' have a total of 4 to 6 carbon atoms, or (ii) R" and R''' together form a heteroalkyl ring having a total of 5 to 7 carbon atoms and a nitrogen atom. By way of example, etidocaine and prilocaine each comprise a chiral center within the definition of the structure of formula (IV), but having different R-groups.

The duration of anesthesia of a local anesthetic may be increased by modifying the chemical structure of the local anesthetic in such a manner as to increase the proportion of the particular local anesthetic which is bound to protein in vivo, for example by adding chemical substituents to the particular local anesthetic molecule which are capable of binding, covalently or non-covalently, to protein moieties.

The therapeutic effects of local anesthetics in the present invention are not directly proportional to their prior art use elsewhere in the body as local anesthetics. Thus, the duration and pain-relieving effects of the local anesthetics in the present invention are enhanced, compared to their use as local anesthetics elsewhere in the body. The enhanced duration and pain-relieving effects of the local anesthetics of the present invention are surprising, compared with the effects achieved using other methods of using local anesthetics.

Dosing Information

The following dosing information is believed to be useful for the methods of the invention for inhibiting pain associated with any of the Disorders of Interest. Dosing information relevant to the systemic drug delivery method of the invention is described separately in the portion of the present disclosure which describes that method.

Various dosage forms may be made which comprise a local anesthetic at a concentration of about 0.01% to about 53% by weight, preferably a concentration of about 0.25% to about 10% by weight, more preferably about 0.5% to about 5% by weight, and even more preferably at about 2.5% by weight. The pharmaceutical composition should be formulated to deliver about 10 micrograms to about 2.5 grams of the local anesthetic to each nostril of a patient, and preferably to deliver about 10 micrograms to about 1 gram. Unit dosage forms containing an amount of the pharmaceutical composition in these ranges may be used. When the pharmaceutical composition is in the form of a liquid for topical application (e.g., a spray), a dose of the pharmaceutical composition may be contained, for example in a volume of about 0.5 milliliters to about 5 milliliters, and preferably in a volume of about 1 milliliter to about 3 milliliters, for delivery to each nostril. Such liquid pharmaceutical compositions preferably contain the local anesthetic at a concentration of about 0.01% to about 20% (w/v), more preferably about 0.25% to about 5% (w/v). When the pharmaceutical composition is in the form of a solid, semi-solid, gel, foam, mousse, cream, emulsion, or the like, the pharmaceutical composition may be formulated to contain about 10 micrograms to about 2.5 grams of the local anesthetic to the patient per nostril in a volume of about 0.5 milliliters to about the capacity of the nasal cavity. In one embodiment, the local anesthetic is dorsonasally administered in a total amount from about 1 milligram to about 70 milligrams (although this amount may alternatively be administered to each nostril), and preferably in an amount from about 10 micrograms to about 50 milligrams. The concentration of the local anesthetic in the solid, semi-solid, gel, foam, mousse, cream, or emulsion form is preferably about 0.1% to about 53% (w/w), more preferably about 0.2% to about 20% (w/w).

A bulk form of a local anesthetic pharmaceutical composition may be made and administered to a patient in one or more doses which comprise the dosage amounts described in the preceding paragraph.

Pharmaceutical Compositions

The local anesthetic pharmaceutical composition that is useful in the methods of the invention may be intranasally or dorsonasally administered in a variety of formulations that can be made readily by one of skill in the art of pharmacology in view of the present disclosure. Formulations which are useful for intranasal administration of the pharmaceutical composition of the invention include, but are not limited to, jelly, cream, gel, foam, mousse, semi-solid, emulsion, sol-gel, foam, a eutectic mixture, liquid, droplet, aerosol, powder, microsomes, liposome, sustained release, degradable polymer, polymer microspheres, impregnated film, fiber, or patch, coated film, fiber, or patch, and other similar dosage forms. The pharmaceutical composition of the invention may contain one or more than one local anesthetic agent. When the pharmaceutical composition contains more than one local anesthetic agent, the agents may be mixed in substantially any ratio such as, for example, a eutectic ratio as described in U.S. Pat. No. 4,562,060. Eutectic mixtures of local anesthetics can be rapidly and more easily taken up by submucosal structures such as nerves, and thus are useful for submucosal nerve block. In addition, levo local anesthetics are vasoconstrictors. Eutectic mixtures of a local anesthetic with a vasoconstricting agent (e.g., a levo local anesthetic) can exhibit prolonged local anesthetic activity and reduced systemic uptake relative to non-eutectic mixtures of the same local anesthetic.

In addition to the local anesthetic, such pharmaceutical compositions may contain pharmaceutically acceptable carriers and other ingredients known to enhance and facilitate drug administration with the additional pharmaceutical agents disclosed herein. Compounds, formulations, and dosages of the additional pharmaceutically active agents described in this method are known in the art. Owing, in part, to the vasodilatory activity of local anesthetics, these compounds may be used according to this method at doses of about half their art-recognized doses to their full art-recognized doses.

Such pharmaceutical compositions may also contain ingredients to enhance sensory acceptability of the composition to a human patient, such as aromatic, aromatherapeutic, or pleasant-tasting substances. The pharmaceutical compositions may also, for example, be made in the form of a flexible solid or semisolid carrier comprising the local anesthetic, such as one of the carriers described in U.S. Pat. No. 5,332,576 or in U.S. Pat. No. 5,234,957; or in the form of suspended micro spheres, such as those described in U.S. Pat. No. 5,227,165. Solid and semi-solid formulations of some local anesthetics are preferred in the compositions, methods, and kits of the inventions, because such preparations improve local anesthetic localization. In these forms, there is less dilution of the local anesthetic by body fluids and less transport of the local anesthetic to an unintended body location. Furthermore, it is believed that these formulations will reduce or minimize unintended side effects such as disagreeable taste, oropharyngeal numbness, dysphasia, and compromise of protective reflexes. In these formulations, a lower amount of local anesthetic may be used, relative to other formulations.

Numerous pharmaceutically acceptable carriers are known in the art, as are methods of combining such carriers with local anesthetics. Examples of such carriers and methods are described, for example, in Genaro, ed., 1985, Remington's Pharmaceutical Sciences, Mack Publishing Co., Easton, Pa., and later editions.

It is understood that the pharmaceutical composition of the invention may comprise a combination of any of the forms described herein. By way of example, microparticles, microsomes, or liposomes comprising a local anesthetic may be suspended in a solution or other formulation of the same or a different local anesthetic, whereby the solution or other formulation provides a rapid onset of anesthesia and the local anesthetic in the form of microparticles, microsomes, or liposomes provides a sustained duration of anesthesia. Sustained release preparations may comprise a slowly-released formulation of a local anesthetic. Inclusion of another local anesthetic in such formulations, in a free or salt (i.e., not slowly-released) form confers to the formulation the ability to act both with a rapid onset of anesthesia and a sustained duration of anesthesia. All such combinations of formulations described herein are included in the invention.

The local anesthetic pharmaceutical composition useful for practicing the invention must be administered in a dose sufficient to inhibit pain associated with any of the Disorders of Interest for at least about one hour, and preferably for at least about two hours. Doses of the local anesthetic pharmaceutical composition may be administered in a single dose, in multiple doses, in sustained release doses, or continuously.

The local anesthetic(s) or other pharmaceutically active agent(s) may be present in the pharmaceutical composition at any concentration from a very dilute concentration through the solubility limit of the local anesthetic or pharmaceutically active agent(s) in the medium in which it is delivered. The local anesthetic(s) or other pharmaceutically active agent(s) may also be present at a concentration greater than the solubility limit of the local anesthetic or pharmaceutically active agent(s) in the medium in which it is delivered by using a crystalline, microcrystalline, or amorphous solid form of the local anesthetic, preferably suspended in a gel, foam, mousse, cream, liquid, liposome, microsome, solid polymeric matrix, or the like. In various embodiments, the local anesthetic may be administered in the form of a eutectic mixture of local anesthetics, such as described in U.S. Pat. No. 4,562,060, in the form of encapsulated or embedded local anesthetic, such as described in U.S. Pat. No. 5,085,868, in the form of an oil-in-water emulsion, such as described in U.S. Pat. No. 5,660,837, or in the form of an emulsion, a cream, a eutectic mixture, or a microemulsion, such as described in International Patent Application Publication No. WO 97/38675, particularly one having thermoreversible gelling properties. Because the nasal cavity is normally cooler than gum pockets, the environment disclosed in International Patent Application Publication No. WO 97/38675, a composition having thermoreversible gelling properties, wherein the composition is a fluid at about 20° C. and a gel or semisolid at the temperature in the human nasal cavity (i.e., about 30-37° C.), is preferred. Any of these compositions may be conveniently delivered dorsonasally and, once so delivered, will be available where placed within the nasal cavity for a sustained period after administration and will spread or drip into other tissues to a lesser degree than would a liquid composition. By using one of these formulations, less of the active compound yields greater therapeutic results and has significantly decreased side effects, such as local and systemic toxicity, tongue and oropharyngeal numbness, discomfort, bad taste, dysphasia, and possible compromise of protective airway reflexes.

Other possible formulations may be made by of one of skill in the art of pharmacology in view of this disclosure without departing from the spirit of the invention. See, for example, (Genaro, ed., 1985, Remington's Pharmaceutical Sciences, Mack Publishing Co., Easton, Pa., and later editions) for a number of forms of typical pharmaceutical compositions that may be adapted readily to the present invention in view of this disclosure.

Co-Administration of Another Therapeutic Agent or Use of the Agent Alone

Numerous pharmaceutically active agents are thought to exhibit their limited therapeutic activity by virtue of the ability of the agent to interact with one or more receptors present on the surface of cerebral blood vessels or other structures. By way of example, migraine therapeutic agents known as serotonin receptor agonists include such agents as sumatriptan and zolmitriptan, and are believed to interact with serotonin receptors. In order to exhibit their pharmacological effects, such agents must gain access by systemic vascular delivery to cerebral blood vessels which have altered vascular flow during an acute migraine episode (Scott, 1994, Clin. Pharmacokinet. 27:33 7-344) and must achieve a critical concentration at the cerebrovascular location of the corresponding receptor(s) in the compromised area. Thus, these pharmaceutically active agents must be administered at the onset of an acute migraine episode in order to avoid the cascade of inflammation that follows initiation of the episode (Limmroth et al., 1996, Curr. Opin. Neural. 9:206-210). Following delivery of one of these agents to the compromised area of a cerebral blood vessel, the concentration of the drug gradually decreases at those sites, and rebound can occur.

Topical local anesthetics are vasodilators and therefore inhibit vasoconstriction, with the exceptions of cocaine, which is a vasoconstrictor. It is believed that the vasodilatory effects of topical local anesthetic administration results from both a direct effect of the anesthetic upon the affected blood vessel and from an indirect effect of the anesthetic upon nerve structures associated with the blood vessel.

In normal states, most blood vessels, particularly those of smaller diameter, do not transport blood because they are not open, due to constriction of blood vessels located proximal thereto with respect to the heart or due to increased muscle tone in the blood vessel wall itself. Should these vessels open at once, profound hypotension would develop immediately, resulting in shock. Many and complex mechanisms are involved in the regulation of blood vessel tone and blood circulation. Hence, in any given tissue or organ, many blood vessels are closed. Blood vessel recruitment refers to a process whereby closed or partially constricted blood vessels are opened or dilated. This increases the number and surface area of blood vessels available for uptake and allows greater blood flow through these vessels. The latter mechanism increases drug transport away, and this decreases local blood drug concentration, favoring drug diffusion into the blood. All of these mechanisms increase drug uptake and transport. Surface vasodilation effected by an intranasally or dorsonasally administered local anesthetic other than cocaine promotes greater blood vessel recruitment and therefore, greater systemic uptake of the pharmaceutically active agent administered in conjunction with the local anesthetic. Hence, coadministration of a local anesthetic and a pharmaceutically active agent results in a more rapid and greater systemic uptake of the pharmaceutically active agent. This produces a more rapid and greater concentration of the pharmaceutically active agent at the affected site.

Furthermore, vasodilation of arterial structures which pass through the intranasal mucosa to feed other relevant neural structures will result in increased delivery of intranasally administered pharmaceutically active agents directly to target sites, especially if arterial blood flows through an area to which the agent and anesthetic are administered. For example, the sphenopalatine artery provides blood supply to much of the middle turbinate of the human nose, to the region of the nasal epithelium overlying the SPG, and to the SPG. Without wishing to be bound by any particular theory, it is believed that the anesthetizing effect of local anesthetics such as bupivacaine induces vasodilation of arterial structures coursing through local tissue on the way to the brain and other relevant neural structures, and increases agent delivery. Additionally, the decreased extracranial and intracranial vasospasm and vasodilation which result from anesthesia of the SPG increases blood flow to relevant structures and therefore increases drug delivery to relevant tissues even further. Hence, intranasal administration of local anesthetic (s) induces both local and intracranial vasodilation and decreases or prevents vasoconstriction caused by normal autoregulatory processes, by neurally mediated processes, or by release of neurotransmitters, neuropeptides, or other factors which are associated with pain or other symptoms of an acute or other type of a Disorder of Interest that is non-CNvD or muscular headache pain. Thus, administration of a local anesthetic to the region of the nasal epithelium overlying the SPG and to other regions of the epithelium located nearby facilitates transport of a pharmaceutically active agent from the surface of the nasal epithelium directly into relevant venous, capillary, and arterial vessels and into the general systemic circulation where intracranial vasodilation or decreased vasospasm results in increased active agent delivery to sites at which it exhibits its pharmaceutical activity.

Therefore, it is anticipated that dorsonasal delivery of a composition which comprises a local anesthetic and a pharmaceutically active agent will result in greater local delivery of the agent to a cerebral neurovascular tissue than could be achieved by dorsonasal delivery of the agent alone, which inhibits a nerve pathway associated with the non-CNvD or muscular headache pain.

Furthermore, if agents, such as sumatriptan and ropivacaine, for example, are believed to have different mechanisms of action, it is believed that the therapeutic effects of the two compounds will be pharmacodynamically synergistic, or at least additive. This is yet another manner that co-administration of a local anesthetic and another pharmaceutical agent is advantageous.

Without wishing to be bound by any particular theory of operation, it is believed that the co-administered compositions inhibit pain or other symptoms and diminish the likelihood that the non-CNvD headache will rebound or recur. This is believed to be especially true for patients who are afflicted with a plurality of distinct non-CNvD headaches or patients who experience separate non-CNvD headache triggers in series.

The present invention includes a method of inhibiting pain associated with any of the Disorders of Interest in a human patient, the method comprising intranasally, and preferably dorsonasally, administering to the patient a composition comprising at least one local anesthetic and a pharmaceutically active agent effective for treatment of the pain, whereby intranasal, and preferably dorsonasal, administration of the composition results in improved uptake of the pharmaceutically active agent by a cerebral neurovascular tissue of the patient and to enhancement of the pharmaceutical activity of the agent.

By way of example, when the pain, such as facial pain, gives rise to a secondary symptom, compositions for inhibiting the secondary symptom and co-administering a suitable pharmaceutically active agent include a sustained release formulation of a composition comprising sumatriptan (e.g., IMITREX™, Glaxo-Wellcome Inc., Research Triangle, N.C.) and lidocaine, a composition comprising zolmitriptan (e.g., ZOMIG™, Zeneca Pharmaceuticals, Wilmington, Del.) and bupivacaine, a composition comprising rizatriptan (e.g., MAXALT™, Merck & Co., West Point, Pa.) and ropivacaine, a composition comprising naratriptan (e.g., NARAMIG™, Glaxo-Wellcome Inc., Research Triangle, N.C.) and tetracaine, and a composition comprising a beta blocker and etidocaine.

Further, compositions for inhibiting the facial or other pain include one or more of a local anesthetic, a vasodiator, vasoconstrictor, epinephrine, norepinephrine, phenylephrine, methysergide, propanolol, a calcium channel blocker, verapamil, ergot, an ergotamine preparation, dihydroergotamine, a serotonin agonist, sumatriptan, zolmitriptan, rizatriptan, naratriptan, a chroman compound, aspirin, acetaminophen, a non-steroidal anti-inflammatory drug, caffeine, a narcotic, meperidine, a mast cell degranulation inhibitor, cromolyn sodium, eucalyptol, tetrodotoxin, desoxytetrodotoxin, saxitoxin, an organic acid, a sulfite salt, an acid salt, a glucocorticoid compound, a steroid ester, magnesium or lithium ions, a centrally-acting analgesic, a beta blocker, an agent that increases cerebral levels of gannna-aminobutyric acid, butalbital, a benzodiazepine, valproat, gabapentin, pregabalin, cannabinoid, antepilectic, duloxetine HCl, amphetamine, ADHD agent, divalproex sodium, a tri-cyclic antidepressant, a narcotic analgesic, a muscle relaxant, a tranquilizer, and/or another compound.

The local anesthetic compounds, formulations, dosages, and methods of administration which are useful for this method of the invention are substantially the same as those described herein with respect to inhibiting other non-CNvD or muscular headache pain. Compounds, formulations, and dosages of the other pharmaceutically active agents described in this method are known in the art. Owing, in part, to the vasodilatory activity of local anesthetics, these compounds may be used according to this method at doses of about half their art-recognized doses to their full art-recognized doses.

The composition may comprise a local anesthetic and a pharmaceutically active agent which is effective for treating non-CNvD or muscular headache pain. By way of example, such a composition may comprise ropivacaine and an additional ingredient. The additional ingredient may, for example, be a serotonin receptor agonist, including, but not limited to, a triptan, e.g., sumatriptan or a chroman compound such as one of the compounds described in U.S. Pat. Nos. 5,387,587; 5,420,151; 5,639,772; and 5,656,657, a non-steroidal anti-inflammatory drug, an anti-emetic, or a mast cell degranulation inhibitor such as cromolyn sodium.

In addition, the composition may comprise an agent which increases or prolongs either or both of the anesthetic effect and the tissue uptake of the local anesthetic. Such agents include, for example, ann-glycofurol compound, such as one of the compounds described in U.S. Pat. No. 5,428,006, eucalyptol, a toxin such as tetrodotoxin, desoxytetrodotoxin, or saxitoxin, an organic acid, a sulfite salt, an acid salt, magnesium or lithium ions, and a centrally-acting analgesic.

In addition, the composition may be a combination of a beta blocker and a local anesthetic, as described, for example, in European Patent No. 754060. The agent may also be a drug that increases cerebral levels of gamma-aminobutyric acid (GABA), either by increasing GABA synthesis or decreasing GABA breakdown. Such GABA-affecting agents include, for example, butalbital, benzodiazepines, valproat, gabapentin, and divalproex sodium. The agent may also be an agent effective for treatment or prevention of neurodegenerative disorders such as, for example, (S)-alpha-phenyl-2-pyridineethanamine (S)-malate, as described in European Patent No. 970813. Furthermore, the agent may be a compound which decreases inflammation, including, for example, a glucocorticoid compound such as a steroid ester. Compounds, formulations, and dosages of vasoconstrictors and other pharmaceutically active agents described in this method are known in the art. Owing, in part, to the vasodilatory activity of local anesthetics, each of these compounds may be used according to this method at doses of about half their art-recognized doses to their full art-recognized doses.

In a patient refractory to monotherapy or treatment using a local anesthetic composition comprising only one additional compound, the composition may be combined with one, two, or more additional compounds, and this combined composition may prove to have therapeutic effects which are synergistic, or at least additive, with respect to each of the individual ingredients. By way of example, such a combined composition may comprise a local anesthetic, a beta-blocker, and a serotonin receptor agonist. Other examples include a combined composition comprising a local anesthetic and an anti-epileptic compounds such as phenytoin sodium (e.g., Dilantin®, Parke-Davis, Morris Plains, N.J.), a combined composition comprising a local anesthetic and a serotonin receptor agonist, a serotonin subclass 5HT1F receptor agonist, LY334,370, and a combined composition comprising a local anesthetic and a sesquiterpene lactone (e.g., a compound such as parthanolide, obtained from an herb such as fever few {*Tanacetum parthenium*}).

Methods of Effecting Intranasal or Dorsonasal Administration

Intranasal administration of a composition may be effected by any method by which the composition is provided to any portion of the nasal epithelium. Intranasal administration of a composition comprising a local anesthetic according to certain methods of the invention is preferably effected by dorsonasal administration of the local anesthetic.

Dorsonasal administration of a pharmaceutical composition may be effected by any method or route which results in delivery of the composition to a tissue, fluid, or surface of a human, whereby a component of the composition is provided to a DnNS either directly or by diffusion through tissue or fluid interposed between the DnNS and the site of administration. For example, dorsonasal administration of a composition comprising a local anesthetic may be effected by injecting a composition directly into a DnNS or by topically applying the composition to a tissue located in close anatomic proximity to the SPG, whereby the local anesthetic is capable of diffusing from the tissue to a DnNS such as the SPG. Topical dorsonasal administration may be accomplished by an intranasal route or by an oropharyngeal route, for example. As described herein, nasal drip methods, nasal spray application methods, and mechanical application methods may be used to effect topical dorsonasal administration of a composition comprising a local anesthetic.

Intranasal administration of the composition of the invention may be improved if the nasal cavity is rinsed, Treated with a decongestant, or otherwise cleared of material which might impede intranasal delivery prior to administration of the composition.

As described in Example 1 of my U.S. Pat. No. 6,432,986, dorsonasal administration of ropivacaine to patients afflicted with migraine using an intranasal spray method, an intranasal drip method, or an intranasal cotton swab method yielded different response rates and different values for the efficacy of ropivacaine for relief of migraine. Although drip and spray methods resulted in wider ropivacaine distribution within the nasal cavity, direct application of ropivacaine to the region of the nasal epithelium overlying the SPG using a cotton swab yielded the most rapid and most effective inhibition of migraine. Similar effects would be expected for treating non-CNvD or muscular headache pain.

The pharmaceutical composition that is useful in the methods of the invention may be administered topically in the types of formulations noted herein. Intranasal, and preferably dorsonasal, administration of the composition may be achieved by providing a mist or aerosol spray comprising the composition to the nasal cavity via the nostril, by providing drops or a stream of liquid comprising the composition to the nasal cavity via the nostril or by injection of the liquid using a hypodermic needle which penetrates the facial skin of the patient, by directly applying the composition dorsonasally using a flexible or anatomically-shaped applicator inserted through the nose or mouth of the patient, including an applicator or implant which is left in place over a period of time, by introducing into the nasal cavity a liquid, gel, semi-solid, powder, or foam comprising the composition, or by any other means known to one of skill in the art of pharmaceutical delivery in view of this disclosure.

Intranasal, and preferably dorsonasal, administration of a pharmaceutical composition to a human has distinct advantages relative to other routes of administration. By administering a composition intranasally or dorsonasally, a high local concentration of the composition in a relevant neural structure, and possibly in the cerebral neurovasculature, may be achieved relative to the systemic concentration of the composition. Local delivery is advantageous in situations in which systemic exposure to the composition is undesirable, either because the composition is metabolized systemically or because systemic exposure results in harmful symptoms. By way of example, systemic administration of a local anesthetic such as bupivacaine is undesirable because bupivacaine is metabolized in the liver and because systemic administration of a relatively large amount of bupivacaine is known to cause serious adverse effects.

Another advantage of intranasal or dorsonasal administration of a compound, at least where local cerebral neurovascular delivery is desired, is that a lesser amount of drug may be administered than would be necessary to administer via a different route. Absorption of intranasally or dorsonasally delivered drug into cerebral neurovascular tissue enables the patient to avoid digestive or at least some hepatic drug metabolism which could occur, for instance, if the drug were administered orally. Furthermore, intranasal or dorsonasal delivery of a drug requires less intensive intervention by a medical professional than some other delivery methods, such as intravenous delivery. Self-medication by an intranasal or dorsonasal route is practical, as evidenced by the many nasal and pulmonary delivery devices and drug formulations which are commercially available.

DnNSs may not be directly accessible via the nasal cavity. However, because of the anatomic proximity of DnNSs to the nasal epithelium, anesthesia of a DnNS can be effected by topical administration of a local anesthetic to the region of the nasal epithelium overlying the SPG or to the region of the nasal epithelium near that region. For example, within the nasal cavity, the SPG lies dorsal to the posterior tip of the middle concha, and is covered by the nasal epithelium at a variable depth of one to nine millimeters (Sluder, 1908, N.Y. State J. Med. 27:8-13; Sluder, 1909, N.Y. State J. Med. 28:293-298). Thus, a compound applied to the surface of the nasal epithelium at or near the region of the nasal epithelium overlying the SPG, such as the surface of the nasal epithelium dorsal to the posterior tip of the middle concha can diffuse through the epithelium and any intervening tissue or fluid to reach the SPG.

The SPG, which is sometimes designated the pterygopalatine ganglion, is located in the pterygopalatine fossa of the human skull, close to the sphenopalatine foramen and close to the pterygoid canal. The SPG is situated below the maxillary nerve where the maxillary nerve crosses the pterygopalatine fossa. Although it is also connected functionally with the facial nerve, the SPG is intimately related with the maxillary division of the trigeminal nerve and its branches. The parasympathetic root of the SPG is formed by the nerve of the pterygoid canal, which enters the SPG posteriorly. The fibers of the parasympathetic root of the SPG are believed to arise from a special lacrimatory nucleus in the lower part of the pons and run in the sensory root of the facial nerve and its greater petrosal branch before the latter unites with the deep petrosal branch to form the nerve of the pterygoid canal. The sympathetic root of the SPG is also incorporated in the nerve of the pterygoid canal. The fibers of the sympathetic root of the SPG are postganglionic, arise in the superior cervical ganglion, and travel in the internal carotid plexus and the deep petrosal nerve. The vidian nerve is located in close proximity to the SPG, and the efficacy of local anesthetics for inhibiting an acute non-CNvD may arise, in whole or in part, from anesthesia of the vidian nerve or another DnNS located in close anatomic proximity to the SPG. It is also known that the trigeminal nerve has anatomical and functional relationship(s) to cervical nerve 2. Other DnNSs which are located in close anatomic proximity to the SPG include, but are not limited to, the cavernous sinus ganglion, the carotid sinus ganglion, numerous branches of the maxillary nerve, the ethmoidal nerve, and the ethmoidal ganglion.

The ability of a compound to diffuse from the surface of the nasal epithelium to a DnNS such as the SPG depends, of course, on the ability of the compound to diffuse through bodily tissues and fluids. Thus, compounds to be delivered to a DnNS by topical application to the nasal epithelium are preferably diffusible through both aqueous solutions and lipids.

Local anesthetics which are related to the class of local anesthetics designated aminoacyl local anesthetics exhibit both suitable aqueous solubility and suitable lipid solubility for use in the methods of the invention. It is believed that such local anesthetics are able to diffuse into nerves in their neutral, uncharged state, and that such local anesthetics assume their pharmacologically active, charged state within nerve cells.

In the case of delivery of a local anesthetic to a DnNS such as the SPG via topical application of the anesthetic to the nasal epithelium, it is preferable that the anesthetic be sufficiently diffusible through bodily tissues and fluids and have a sufficiently long half-life in vivo that the anesthetic is able to diffuse from the epithelium to the DnNS in an amount and for a duration sufficient to anesthetize the DnNS or otherwise inhibit the physiological processes that result in one or more symptoms of non-CNvD or muscular headache pain, such as a period on the order of at least about one hour, and preferably at least about two hours. On the other hand, the diffusivity through bodily tissues and fluids and the in vivo half-life of the anesthetic must not be so high and long, respectively, that the anesthetic is delivered systemically in an amount sufficient to cause the adverse effects known to be associated with systemic administration of local anesthetics (see, e.g., Physician's Desk Reference®, Medical Economics Co., Inc., Montvale, N.J., 51st ed., 1997, pp. 424-427, and later editions).

Apparatus for Intranasal or Dorsonasal Administration of a Composition

Particularly contemplated apparatus for intranasal or dorsonasal delivery of a composition to a human patient according to the methods of the invention include, but are not limited to, an anatomically-shaped applicator, a metered dose dispenser, a non-metered dose dispenser, a squeezable dispenser, a pump dispenser, a spray dispenser, a foam dispenser, a powder dispenser, an aerosol dispenser, a dispenser containing a propellant, an inhalation dispenser, a patch comprising the composition, an implant comprising the composition, a soft pipette with an elastomeric bulb in fluid communication with a reservoir containing the composition, a dropper for directing the composition past the conchae of the patient to an intranasal nerve structure (InNS, including a DnNS, but not limited to DnNSs), or intranasal blood vessel (InBV), a swab having an absorbent portion impregnated with the composition, a swab having an anatomically-shaped portion comprising an absorbent portion impregnated with the composition, and a swab having a compressed absorbent portion in fluid communication with a reservoir containing the composition. An anatomically-shaped applicator is one which has a shape which permits insertion of the applicator into the nose or mouth of a human and which enables contact of the composition delivered by the applicator with the surface of the region of the nasal epithelium overlying the InNS or with a surface of the nasal epithelium near the region of the nasal epithelium overlying the InNS (e.g., a DnNS such as the SPG). It is preferred that the shape and/or materials of the apparatus be selected for comfortable insertion or application via an intranasal route. The apparatus preferably is adapted to contact either a superior portion of the nasal epithelium or a portion of the nasal epithelium that overlies a DnNS.

Another embodiment of an apparatus for intranasal or dorsonasal delivery of a pharmaceutical composition of the invention comprises a body having a plurality of passages through which a composition may be delivered. The device may be designed so that the pharmaceutical composition of the invention is delivered through each passage, the passages being individually or collectively connected to, for example, a plurality of orifices in an anatomically-shaped applicator whereby the orifices direct delivery of the composition to a plurality of locations within the nasal cavity when the applicator is inserted into the nose of a patient and operated. The device may alternately be designed so that the pharmaceutical composition of the invention is delivered through one or more passages and an additional pharmaceutically active agent is delivered through the same passages or through one or more different passages. Alternately, the device may comprise components of the pharmaceutical composition of the invention which are separately delivered through one or more passages of the device and mixed either in a passage of the device or in the nasal cavity of the patient.

Devices which contain, deliver, or produce a semisolid local anesthetic composition are contemplated. To use one of these devices, an outlet of the device is situated in fluid communication with one of or both of the nostrils of a patient. A solid, foam, semi-solid, foam-forming fluid, or another fluid which exhibits an increase in viscosity upon administration, such as one of the type known in the art, is provided to the outlet, whereby it passes into the nostril of the patient, filling or partially filling the nasal cavity. A local anesthetic in the composition contacts the walls of the nasal cavity, preferably in a dorsonasal location, and the local anesthetic is thereby administered to the patient. The devices described herein can be used to deliver substantially any composition or material to the portion(s) of the nasal epithelium for which they are adapted.

Directed Intranasal Drug Delivery Devices

There are several known devices for effecting intranasal delivery of a drug or other non-gaseous pharmaceutically acceptable preparation. Such devices include, for example, liquid-containing squeeze bottles, liquid-containing pressurized containers, liquid-containing pump-type containers, droppers, microtine powder dispersers, and nebulizers. Although each of these prior art devices may be used to intranasally administer a pharmaceutical composition (e.g., according to any of the methods described herein), each of these devices has certain drawbacks and shortcomings which make their use for directed intranasal administration of compositions (e.g., for dorsonasal administration) sub optimal.

Liquid-containing squeeze bottles dispense atomized liquid upon pressurization of the bottle effected by squeezing. However, the amount of liquid expelled upon squeezing, the direction in which the liquid is expelled, and the velocity at which it is expelled can vary quite considerably based on how the user manipulates the device. Furthermore, the degree of atomization (i.e., the size of the droplets) may depend on the force applied to the container.

Liquid-containing manual pump-type containers dispense atomized liquid upon actuation by the user of a pump mechanism, in which displacement of a portion of the container along a vertical axis of the container causes atomized liquid to be expelled from a second portion of the container, generally in a direction parallel to the longitudinal axis of the container. By inserting the second portion into a nostril and actuating the pump, a stream or mist of atomized liquid is expelled into the nostril. These devices, like the other prior art devices, exhibit significant variability in the direction in which the liquid is expelled, owing to variation in the positioning of the device by the user. Furthermore, because these devices are operated by applying pressure to the device in a direction toward the interior of the nostril, these devices are uncomfortable and present the possibility of injury due to accidental excessive applied force or misplacement by the distressed user.

Liquid-containing pressurized containers dispense atomized liquid upon manipulation by the patient of a triggering mechanism. For example, many such devices comprise a valve through which atomized or liquid medication is expelled upon depressing a trigger or other actuator to open the valve. Although these containers may exhibit improved control over the amount and velocity of expelled fluid, relative to squeeze bottles, the intranasal direction in which the liquid is delivered depends heavily on actions of the user.

Droppers, pipettes, and other bulk liquid instillation devices share the drawback that either the patient must remain in an awkward position (e.g., lying on the back, with the head propped up and to one side) in order to retain the liquid in the nasal cavity for an appreciable period or, alternatively, that administration must be repeated numerous times, owing to rapid drainage of the liquid from the nasal cavity. In addition, instillation of bulk liquid into the nasal cavity presents the risk that the liquid will be inhaled by the patient into the lungs or passed through the nasopharynx into the esophagus and digestive system. This increases uncomfortable numbness and potentially compromises protective airway and swallowing reflexes. Furthermore, increased wastage leads to increased systemic levels of drug and decreased desired local effects.

Micro fine powder dispersers and nebulizers may be used to deliver powders and atomized liquids, respectively, to the nasal epithelium, but share a number of drawbacks. First of all, the pattern of delivery will largely parallel the pattern of inhalative air flow through the nasal cavity, and therefore may not distribute the agent evenly to the nasal epithelium, particularly to more remote regions, such as the dorsonasal region or a superior portion of the nasal epithelium. Second of all, a significant portion of inhaled powder and mist bypasses the nasal epithelium altogether, and instead is carried, along with bulk inhaled air, into the bronchi and lungs. When systemic delivery of a compound is desired, such bypass may be desirable. However, when local directed intranasal (e.g., dorsonasal) administration is desired, this bypass may frustrate effective delivery.

All of these prior art drug delivery devices share a common shortcoming. Each disperses the drug non-specifically to the nasal epithelium and does not target local areas such as those overlying a nerve structure (e.g., a portion of the nasal epithelium including or overlying a branch of an InNS such as the olfactory nerve or another DnNS such as the SPG, a ciliary blood vessel, or ciliary nerve), those overlying an intranasal blood vessel, or the nasal cavity orifices of the smuses.

The shortcomings of the prior art drug delivery devices may be understood in view of the fact that directed administration of compositions to selected remote areas of the nasal epithelium (e.g., the dorsonasal region or a superior portion of the nasal epithelium) has not previously been demonstrated. Prior art intranasal drug delivery methods have generally taught administration to the largest possible portion of the intranasal epithelium, in order to provide the drug to much of the intranasal epithelium. In contrast, as described herein, several of the methods of the invention teach that dorsonasal, or other intranasally-targeted, administration of a pharmaceutical composition (e.g., a composition comprising a local anesthetic) may be preferable for a number of reasons. Intranasal administration of compositions to portions of the nasal epithelium overlying an InNS or an InBV can deliver a pharmaceutically-active (i.e., pharmacologically-active or biologically-active) agent to the InNS or InBV, or to another tissue that communicates therewith. For example, intranasal administration of a composition to a portion of the nasal epithelium overlying an InBV can be used to effect systemic administration (or local vascular delivery) of the agent, and intranasal administration of a composition to a portion of the nasal epithelium overlying an InNS can be used to effect delivery of the agent to another nerve structure (e.g., a cephalic ganglion, the spinal cord, or a portion of the brain) with which the InNS connects.

First, it is believed that the site at which local anesthetics have their biological effect may be physically located at or in close proximity to the portion of the nasal epithelium to which an intranasally administered composition is applied (i.e., as described elsewhere herein, for example, to the region of the nasal epithelium overlying the SPG for a dorsonasally administered local anesthetic); thus, dorsonasal administration may be preferable to general intranasal administration because it directs the pharmaceutically active agent to or near its site of action for treatment of non-CNvD or muscular headache pain.

Second, site-directed (e.g., dorsonasal) administration may be used to intentionally limit intranasal delivery of the biologically active agent to non-desired intranasal sites, thereby minimizing uptake of the biologically active agent into the bloodstream. This may be particularly important with biologically active agents (e.g., dextro-bupivacaine) which, at high bloodstream concentrations of the agent, have undesirable side-effects are used.

Third, because directed intranasal administration limits uptake of the administered agent into the bloodstream, the agent may be delivered (e.g., to a dorsonasal nerve structure) more frequently and at a higher concentration or greater amount than it could if it were administered in a more anatomically diffuse way. Therefore, high concentrations of the agent may be achieved in a tissue (e.g., the SPG, cerebrospinal fluid, or a brain or other CNS structure) located at or in close proximity to the dorsonasal epithelium. When the agent has a biological activity which decreases over time (e.g., a local anesthetic), administration of a high local concentration of the agent may prolong the duration of the intended biological effect.

Fourth, with intranasal administration of a compound having an uncomfortable, but non-harmful, side-effect (e.g., numbness), it may be preferable to limit the exposure to the compound to the type or the amount of tissue which exhibits the side effect by administering the compound only, or preferentially, to a selected portion of the nasal epithelium (e.g., dorsonasally), thereby limiting the side-effect upon non-targeted tissues.

Other advantages of directed intranasal administration, in contrast to general intranasal administration will also be understood by the skilled artisan in view of the present disclosure.

The disadvantages of older intranasal administration devices may be overcome, and the advantages of more effective dorsonasal and other site-directed intranasal administration may be achieved by using the devices disclosed in prior U.S. Pat. Nos. 6,491,940 and 7,799,337, the disclosures of which are hereby incorporated herein by reference in their entireties.

Kits of the Invention

The invention additionally includes a kit comprising a local anesthetic pharmaceutical composition, as described herein, and an applicator, as also described herein, for intranasally, and preferably dorsonasally, administering the composition to a human patient to inhibit any of the Disorders of Interest. The kit is used by administering the composition to the patient at a time when the patient is experiencing a symptom of any of the Disorders of Interest or a prodromal symptom thereof. The kit may further comprise another pharmaceutically active agent, another local anesthetic, and the like. The kit may, and preferably does, further comprise instructional material which describes directed intranasal (e.g., dorsonasal) administration of the composition to a patient. The instructional material may, for example, comprise written instructions to intranasally or dorsonasally administer the composition included in the kit in accordance with this invention.

The kit described herein may also comprise devices using any of the Stimulation Techniques, including any external or implantable device, and any device that may be used extracorporeally to activate the implanted device, and instructional material which describes their use.

Certain embodiments of the invention is now described with reference to the following Examples. These Examples are provided for the purpose of illustration only and the invention should in no way be construed as being limited to these Examples, but rather, should be construed to encompass any and all variations which become evident as a result of the teaching provided herein.

Example 1

A female patient with pain and decreased range of motion for many months following repair of a torn rotator cuff, was treated using a fanlike injection of lidocaine 1% (3 ml) merely in the vicinity of the suprascapular nerve, hitting small fibers in the area. The patient showed remarkable improvement in pain and range of motion.

This block differs from classic suprascapular block in that the area around the nerve was targeted and treated, rather than the nerve itself. This procedure was easier to perform than trying to block the suprascapular nerve directly, which would have been much more difficult to target or specific, direct treatment. In terms of neurostimulation, or blocking with energy sources such as light, laser, infrasound or electricity, it means that transcutaneous methods can work well by targeting the area around a major nerve, or merely within its general area of innervation, and not necessarily the nerve itself. It also shows that a regional sympathetic block can be achieved merely by infiltrating or injecting an area proximal to the damage and that a more difficult ganglion block or direct nerve injection is not needed. The latter may work synergistically with the field sympathetic block which was demonstrated here.

Example 2

A female patient with severe leg and foot pain for several years due to prior surgical trauma resulting from an initial bunionectomy and other follow-up surgeries was treated by a saphenous nerve injection of ropivacaine 0.25% (5 ml) after exquisite tenderness was noted on palpation of the saphenous nerve greater than 14 cm proximal to the level of her foot trauma. However, much of her symptomatology was in the distribution of other nerves. Indeed, she had motor dysfunction of the toes and her saphenous nerve is a purely sensory nerve. Within 10 minutes, the patient reported almost complete relief of pain and had normalized sensation and strength in the distribution of other peripheral nerves, including the peroneal nerves. She could walk like she had not in many years. Surprisingly, we see that block of one nerve with purely sensory function decreased symptoms across the distribution of other nerves.

Example 3

A female patient with CRPS and severe pain, including pins and needles sensation in her right hand for over 20 years, presented with these symptoms and major discoloration in her right arm due to compartment syndrome many years ago and could barely open and close her fist. After a single treatment with bupivacaine 0.25% (3 ml) in the fanlike distribution of the radial nerve, she felt dramatically better and could open and close her hand and make and maintain a fist. Neurotrophic findings of decreased temperature, edema, allodynia, discoloration and severe restriction of range of motion decreased dramatically. This shows that CRPS of a limb can be treated by a compartment-type of peripheral block not previously done for single peripheral nerves.

Example 4

Figure 4:
FIG. 4 is a photograph of a patient shortly after a traumatic facial injury as set forth in Example 4.
Figure 5:
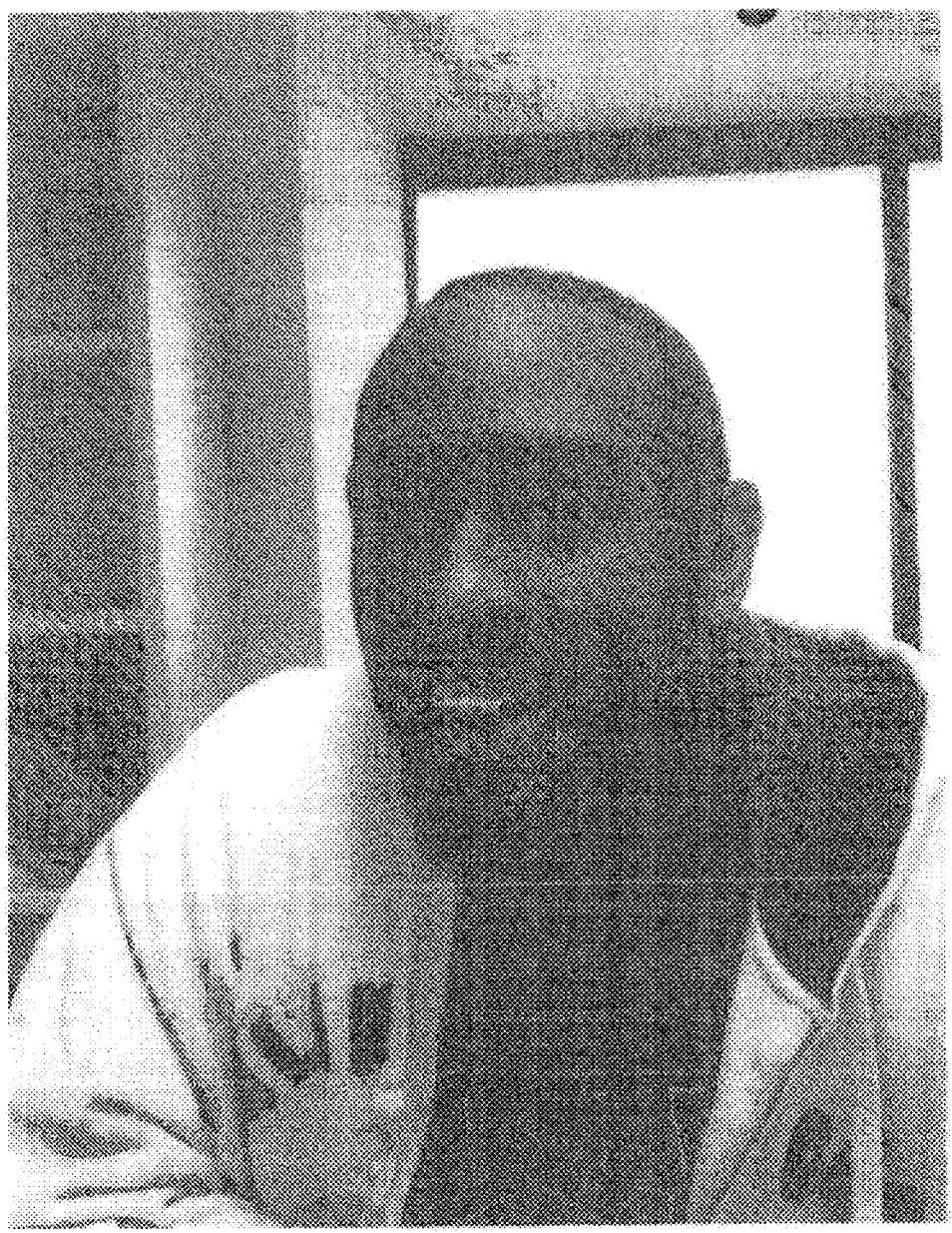
FIG. 5 is a photograph of the same patient shown in FIG. 4 after several months of treatment as set forth in Example 4.

A male patient had severe facial pain following a large metal beam impact which left him with facial neuropathies and headache that adversely affected his ability to eat and speak was treated with intranasal bupivacaine 0.5% (4 ml). The photograph of FIG. 4 shows the patient's condition shortly after the injury. Within 3 minutes, the patient reported almost complete relief of pain and could open his mouth wide, eat normally and could speak for normal periods of time and at normal volume. He improved with subsequent repeat treatments and was able to perform job and daily activities normally. The photograph of FIG. 5 shows the patient after several months of treatment.

Example 5

A male patient with severe facial pain resulting from being hit in the face with a pipe that caused four facial fractures, for seven years had numbness in certain areas of his face and severe pain in the area of his left eye, as well as generalized facial and head pain. He was treated with intranasal bupivacaine 0.5% (4 ml). Within 1 minute, the patient reported remarkable, complete relief of pain.

Example 6

A male patient had sustained facial nerve injuries from a close range gunshot wound to the face. He was in excruciating pain and could not speak or eat without severe duress. Multiple treatments with intranasal bupivacaine 0.5% (3-4 ml) monthly manages his pain well with several years follow up with no adverse sequela. He had been in agony for over 5 years previous to this treatment.

Example 7

Figure 6:
FIG. 6 is a photograph of a patient suffering from severe CRPS of the left arm and hand and related symptoms as set forth in Example 7.
Figure 7:
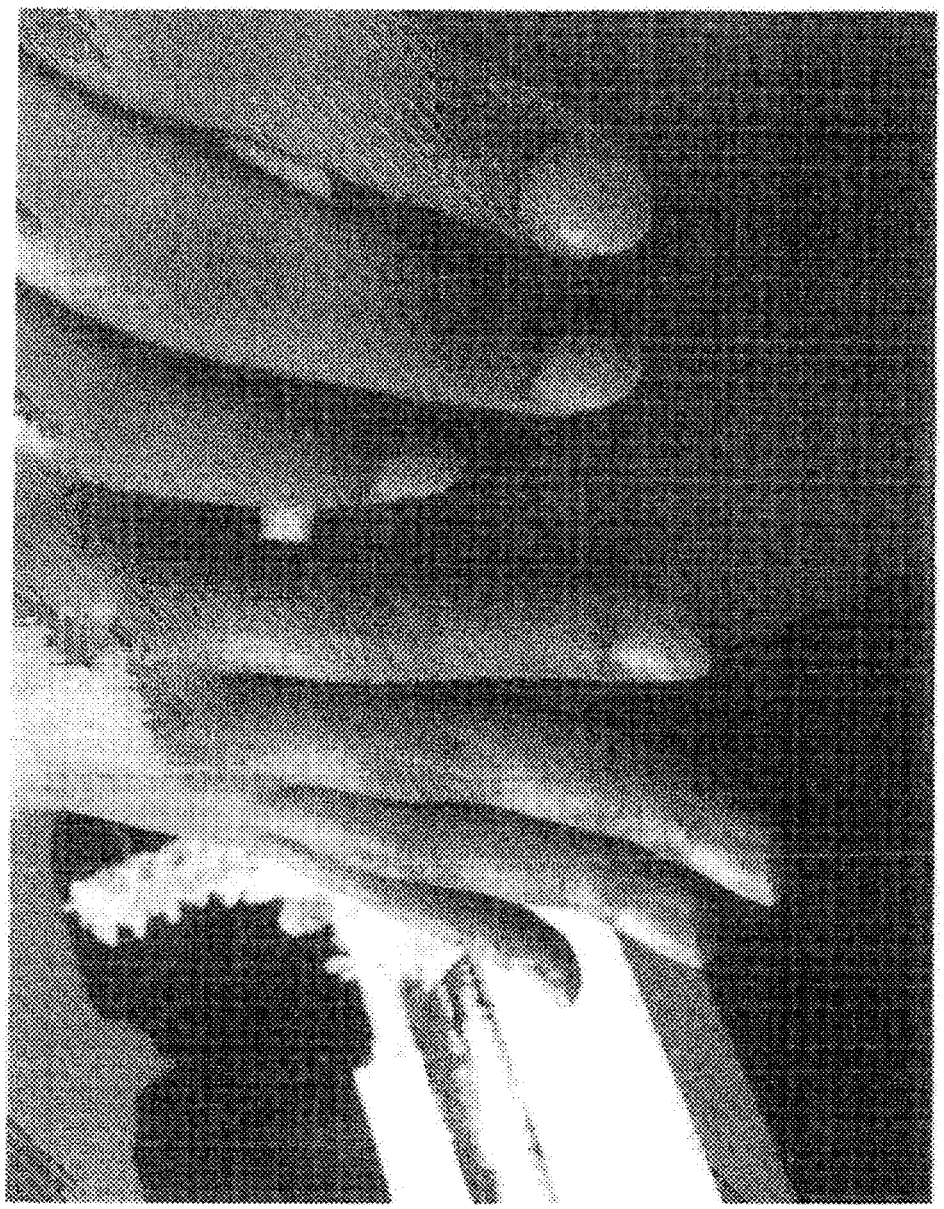
FIG. 7 is a photograph of the hands of the patient shown in FIG. 6 showing some of the symptoms for which she was treated as set forth in Example 7.

A female patient had severe CRPS of the left arm and hand with frozen shoulder syndrome and severe edema, allodynia coldness and nail changes involving her left hand for over 18 months. Her condition is shown in the photographs of FIGS. 6 and 7. She failed all therapies to the time of presentation. Direct suprascapular injection of lidocaine 1% (4 ml) together with methylprednisolone acetate (10 mg) and subsequent fanlike injection in the suprascapular region completely reversed these symptoms and findings in a few treatment sessions.

Example 8

Several patients with facial trauma or trigeminal neuralgia were treated with non-implanted electrical SPG stimulation by nasal insertion of an electrode during flare ups. The treatments decreased pain in these patients.

The Examples are merely exemplary of the types of treatments using specific local anesthetics or devices that could be used according to various embodiments and aspects of the present invention.

Other exemplary embodiments of the invention relate to:

A method of treating complex regional pain syndrome of an upper extremity of a human patient, including or excluding the shoulder, the method comprising administering a local anesthetic agent in the vicinity of the patient's suprascapular nerve.

A method of treating complex regional pain syndrome of a lower extremity of a human patient, the method comprising administering a local anesthetic agent in the vicinity of the patient's nerve of the lower extremities, such as the saphenous, tibial, posterior tibial or sural nerve.

A method of treating complex regional pain syndrome relating to pain and decreased function of an arm or hand of a patient, the method comprising administering a local anesthetic agent in the vicinity of the patient's radial, medial, ulnar or musculocutaneous nerve.

A method of improving a human patient's shoulder's range of motion following injury, trauma, post-surgery, or frozen shoulder syndrome, the method comprising applying a local anesthetic or an anti-neuropathic agent in the vicinity of the patient's suprascapular nerve.

In these other exemplary methods, as well as the specific methods of Examples 1-4, other local anesthetics at other dosages could be administered. For instance, without limitation, about 0.1 ml to about 40 ml of about 0.1% by weight to about 1% by weight of the local anesthetic may administered. Typical exemplary local anesthetics that could be used include, without limitation, lidocaine, bupivacaine, levobupivacaine, ropivacaine, etidocaine, prilocaine, or a eutectic mixture of a local anesthetic. The local anesthetics may be administered in any of the pharmaceutical compositions or dosage forms mentioned above, and preferably by injection (and more preferably by fanlike injection), iontophoresis or topical administration.

Still another embodiment of the invention includes a method of treating complex regional pain syndrome relating to shoulder, arm or hand of a patient, the method comprising directly injecting a local anesthetic and a steroid medication in the patient's suprascapular nerve along with administration of a local anesthetic and a steroid medication in the vicinity of the patient's suprascapular nerve. For instance, without limitation, about 0.1 ml to about 40 ml of about 0.1% by weight to about 1% by weight of the local anesthetic and about 1 mg to about 80 mg of the steroid medication may be injected and administered. Typical exemplary local anesthetics that could be used include, without limitation, lidocaine, bupivacaine, levobupivacaine, ropivacaine, etidocaine, prilocaine, or a eutectic mixture of a local anesthetic. Typical steroid medications that could be used include, without limitation, methylprednisone acetate, betamethasone and hydrocortisone.

Other embodiments of the invention include a method of treating at least one of facial pain, facial neuropathy, decreased eating function or decreased speech function of a patient, the method comprising administering a local anesthetic intranasally to the patient. For instance, without limitation, about 0.1 ml to about 10 ml of about 0.1% by weight to about 2% by weight of the local anesthetic is administered. Typical exemplary local anesthetics that could be used include, without limitation, lidocaine, bupivacaine, levobupivacaine, ropivacaine, etidocaine, prilocaine, or a eutectic mixture of a local anesthetic.

Still another embodiment of the invention includes a method of improving a human patient's shoulder's range of motion following injury, trauma, surgery, or frozen shoulder syndrome, the method comprising applying a Stimulation Technique in the vicinity of the patient's suprascapular nerve.

Another embodiment of the invention includes a method of treating pain of facial trauma of a patient, the method comprising neurostimulation of the patient's sphenopalatine ganglion.

Yet another embodiment of the invention relates to a method of treating pain of trigeminal neuralgia of a patient, the method comprising stimulating the patient's sphenopalatine ganglion.

For any of these additional embodiments involving stimulation, a Stimulation Technique or a Stimulation Device could be used.

For any of the treatments set forth herein, depending on the nature, severity or intensity of the disorder, loss of motor or sensory function, sympathetic tone or range or fluidity of motion, or other condition or symptom, follow-up treatments, which may be more or less frequent, but preferably such as monthly, may be necessary or desirable.

Parenteral nerve block intervention may include any one or more of direct nerve injection, injection in a fanning or fanlike manner (a fan block), segment infiltration block, compartment infiltration, local infiltration, infusion, iontophoresis, patch, or transdermal delivery of any effective agent. The segment infiltration block is easy to do and ultrasound guidance may not be required. The treatment agent or injectate includes but is not limited to local anesthetic, steroid, ketamine, neuropathic agent, anti-seizure medication, antidepressant, stimulant agent, nutritional supplement, amino acid, energy precursor, oxygen, oxygenated substrate, oxygenating substrate, or membrane stabilizer or protectant (such as polyethylene glycol, for example), or a precursor of any of them, in depot or non-depot form.

The internal implanted neurostimulation intervention includes but is not limited to implantation of a temporary or permanent neurostimulator, preferably a miniaturized electronic stimulation device or energy generating device, with a self-contained power unit, or with power induced from an external source, that may be based on or responsive to the patient's muscle activity such as body movement of motion, the patient's metabolism or the patient's chemical environment.

Any of the foregoing interventions may be supplemented with other central or peripheral neurostimulation, or by medication delivery at a proximal location. Alternatively, more distal or other distinct structures may be treated by one or more of these methods to obtain a synergistic effect.

This approach has been quite effective for frozen joint syndromes, CRPS type 2, post compartment syndrome neuropathy, post catheterization femoral neuropathy, and post traumatic neuropathy. It has been effective after several years of severe symptomatology. Further, it has been effective in a few patients with severe subjective symptomatology, particularly pain and decreased range of motion, without clear pathology. In these, CRPS was a possible etiology.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of improving a human patient's shoulder's range of motion following injury, trauma, post-surgery, or frozen shoulder syndrome, the method comprising externally applying an electrical potential or current or electromagnetic radiation to at least one locus to the patient's suprascapular nerve structure, or applying a Stimulation Technique to the patient's suprascapular nerve structure, wherein the Stimulation Technique is applied by a nonimplanted Stimulation Device retained on the patient by a dressing or appliance in the vicinity of the patient's suprascapular nerve.

* * * * *